US008834843B2

(12) United States Patent
Newton et al.

(10) Patent No.: US 8,834,843 B2
(45) Date of Patent: *Sep. 16, 2014

(54) IMAGING METHOD

(75) Inventors: Ben Newton, Amersham (GB); Salah Chettibi, Amersham (GB); Magne Solbakken, Skien (NO)

(73) Assignee: GE Healthcare Limited, Buckinghamshire (GB)

(*) Notice: Subject to any disclaimer, the term of this patent is extended or adjusted under 35 U.S.C. 154(b) by 182 days.

This patent is subject to a terminal disclaimer.

(21) Appl. No.: 12/742,984

(22) PCT Filed: Nov. 19, 2008

(86) PCT No.: PCT/EP2008/065824
§ 371 (c)(1),
(2), (4) Date: May 14, 2010

(87) PCT Pub. No.: WO2009/071444
PCT Pub. Date: Jun. 11, 2009

(65) Prior Publication Data
US 2010/0316565 A1 Dec. 16, 2010

Related U.S. Application Data

(60) Provisional application No. 60/988,840, filed on Nov. 19, 2007.

(30) Foreign Application Priority Data

Nov. 19, 2007 (GB) .................... 0722650.9

(51) Int. Cl.
*A61K 49/00* (2006.01)
*A61K 49/14* (2006.01)
*A61K 51/08* (2006.01)
*A61K 49/08* (2006.01)

(52) U.S. Cl.
CPC ............... *A61K 49/14* (2013.01); *A61K 51/082* (2013.01); *A61K 49/0004* (2013.01); *A61K 49/085* (2013.01); *A61K 51/08* (2013.01)
USPC ......... 424/9.2; 424/1.11; 424/1.65; 424/1.69; 424/1.81; 424/9.1

(58) Field of Classification Search
CPC ... A61K 51/082; A61K 51/088; A61K 51/08; A61K 51/00; A61K 51/02; A61K 51/04; A61K 51/06; A61K 51/065; A61K 38/00; A61K 38/04; A61K 38/08; A61K 38/12; A61K 38/085; A61K 2121/00; A61K 2123/00; A61K 49/0004; A61K 49/0008; A61K 49/00; A61K 49/0017; A61K 49/0019; A61K 49/0021; A61K 49/0052; A61K 49/0054; A61K 49/0056; A61K 49/04; A61K 49/06; A61K 49/08; A61K 49/085; A61K 49/10; A61K 49/12; A61K 49/14; C07K 4/00; C07K 7/00; C07K 7/02; C07K 7/50; C07K 7/14
USPC ........... 424/1.11, 1.65, 1.69, 1.81, 1.85, 1.89, 424/9.1, 9.2, 9.3, 9.34, 9.36, 9.4, 9.42, 9.5, 424/9.6, 9.7; 530/300, 316, 327, 328; 514/1, 1.1

See application file for complete search history.

(56) References Cited

U.S. PATENT DOCUMENTS 7,811,551 B2  10/2010 Cuthbertson et al.
8,299,030 B2  10/2012 Cuthbertson

FOREIGN PATENT DOCUMENTS

| WO | 2006/054904 |   | 5/2006 |
|----|-------------|---|--------|
| WO | WO 2006/054904 | * | 5/2006 |
| WO | 2006/073314 |   | 7/2006 |
| WO | 2006/115416 |   | 11/2006 |
| WO | 2007/066115 |   | 6/2007 |
| WO | 2007/148074 |   | 12/2007 |

OTHER PUBLICATIONS

The Journal of Pharmacology and Experimental Therapeutics, 2007, vol. 322, pp. 560-568.*
Bataller et al, Journal of Clinical Investigations, 2005, vol. 115, pp. 209-218.*
Christelle, et.al. "The Common Bile Duct Ligation in Rat: A Relevant in Vivo Model to Study the Role of Mechanical Stress on Cell and Matrix Behaviour" Histochemistry and Cell Biology, Springer, Berlin, DE., vol. 126, No. 4, Apr. 20, 2006 pp. 517-523.
Haubner, et.al. "Radiolabeled AlphaVbeta3 Integrin Antagonists: A New Class of Tracers for Tumor Targeting" Journal of Nuclear Medicine, Society of Nuclear Medicine, Reston, VA, US vol. 40, No. 6, Jun. 1, 1999, pp. 1061-1071.
Indrevoll, et.al. "NC-100717 A Versatile RGD Peptide Scaffold for Angiogenesis Imaging" Bioorganic & Medicinal Chemistry Letters, Pergamon, Elsevier Science, GB. vol. 16, No. 24, Dec. 15, 2006 pp. 6190-6193.
Du, et.al. "Cyclic ARG-GLY-ASP Peptide-Labeled Liposomes for Targeting Drug Therapy of Hepatic Fibrosis in Rats" Journal of Pharmacology End Experimental Theraeutics, vol. 322, No. 2, 2007 pp. 560-568.
EP2008/065824 ISRWO Dated Nov. 9, 2009.

* cited by examiner

*Primary Examiner* — D L Jones

(57) ABSTRACT

The present invention relates to a method useful in facilitating the identification of fibrogenesis in a subject. The method of the invention is particularly useful when applied as part of a method to diagnose fibrogenesis of the liver. The invention also provides a compound for use in a method for identification of fibrogenesis in a subject A further aspect of the invention is a compound for use in the preparation of a medicament for use in a method for identification of fibrogenesis in a subject.

13 Claims, 5 Drawing Sheets

IMAGING METHOD

This application is a filing under 35 U.S.C. 371 of international application number PCT/EP2008/065824, filed Nov. 19, 2008, which claims priority to United States provisional application number 60/988,840 filed Nov. 19, 2007 and Great Britain application number 0722650.9 filed Nov. 19, 2007, the entire disclosure of each of which is hereby incorporated by reference.

TECHNICAL FIELD OF THE INVENTION

The present invention relates to an in vivo imaging method and in particular to a novel application of certain known in vivo imaging agents. Preferred methods of in vivo imaging of the invention are single-photon emission tomography (SPECT) and positron-emission tomography (PET).

DESCRIPTION OF RELATED ART

There is a wide geographic distribution and high prevalence of insults with the potential to cause liver fibrosis; including chronic viral hepatitis, non-alcoholic steatohepatitis (NASH), parasitemia, inborn errors of metabolism, and toxic damage through alcohol consumption. All these factors mean that fibrosis, leading to cirrhosis and possible cancer of the liver, remains a major cause of morbidity and mortality worldwide. In the United Kingdom alone, liver disease is now the fifth most common cause of mortality, and its incidence is rising (Iredale 2003 BMJ Vol. 327 pp 143-147).

Two types of fatty liver disease exist; non-alcoholic fatty liver disease (NAFLD), and NASH. Around 24% of the US population is thought to have NAFLD, which progresses to NASH at low frequency. NAFLD is associated with the metabolic syndrome, which is linked with obesity, hyperlipidemia, hypertension and type II diabetes. It is believed that in the region of 47 million individuals in USA has the metabolic syndrome. An estimated 8.6 million of the US population are thought to have NASH, which may become associated with fibrosis and cirrhosis with 20-28% of patients with NASH developing cirrhosis over a decade. NAFLD is therefore very common and represents the less severe end of a spectrum of NAFLD that may progress to NASH, and ultimately to cirrhosis of the liver. Liver fibrosis is an indicator of a risk of progression from NASH to cirrhosis.

Currently-used approaches for the detection of liver fibrosis have some notable disadvantages. Liver biopsy analysed histologically for the pattern of collagen deposition is considered the gold standard for assessing liver disease stage and liver fibrosis. However, the procedure is associated with some morbidity, occasional mortality, high costs, sampling errors and high inter-observer variability among hepatopathologists in categorising the degree of fibrosis. Sampling of liver in biopsy results in only 1/50,000th of the liver being assessed, which can lead to errors in stage diagnosis. Furthermore, as collagen is a marker of fibrotic tissue it is not an ideal target for active disease as it can be found both in the later stages of active fibrosis as well as where the disease process is resolving. There is currently no means by which liver fibrosis can effectively be characterized and monitored via a non-invasive procedure. This has a negative impact on early therapeutic intervention which may slow or halt liver fibrosis. Furthermore, in order to monitor disease progression in a timely manner, it is recommended to carry out repeat biopsies every 3-5 years. Available blood tests for detecting liver fibrosis are of limited value because they cannot be used for assessing the degree of fibrosis or for discriminating fibrosis from cirrhosis. Therefore there is no currently available method that can distinguish NAFLD from NASH, or satisfactorily quantify and characterise fibrosis in NASH.

Hepatic stellate cells (HSC) are widely regarded as the principal fibrocompetent cell in the liver. During progressive liver fibrosis, HSC activate and proliferate, but during resolution of fibrosis there is extensive HSC apoptosis that coincides with degradation of the liver scar. This progressive stage of the process of fibrosis is termed fibrogenesis. An upregulation of integrin expression on activated HSC has been reported (Zhou et al J. Biol. Chem. 2004; 279(23): 23996-24006). Activation of HSC is critical to the initiation and development of fibrogenesis and subsequently liver fibrosis. Markers of HSC activation therefore represent targeting opportunities for the imaging of fibrogenesis. In this regard, markers of the process that have recently become prominent are integrins (Zhou et al 2004 J. Biol. Chem.; 279: 23996-24006; Patsenker et at 2007 J. Hepatol.; 46(5): 878-887; Zhou et al 2006 J. Biol. Chem.; 281: 39757-39765; Carloni et al 1996 Gastroenterology: 110: 1127-36).

The use of suitably labelled integrin binders for in vivo imaging applications has previously been described.

WO 2004/020435 discloses integrin-binding piperidinyl compounds that are useful in the treatment of diseases associated with pathological upregulation or disregulation of cell proliferation resulting from expression of $\alpha_v$ integrin, or subtype thereof. WO 2004/020435 also discloses that the compounds of the invention may be conjugated to a moiety suitable for in vivo imaging, and used as a non-invasive tumour imaging agent.

WO 2007/088041 discloses a class of small molecule integrin-binding compounds that are useful in the treatment and/or prevention of a disease, wherein the disease is preferably one mediated by $\alpha_v\beta_1$ integrin. Liver fibrosis is included as a particular disease where the compounds of WO 2007/088041 find use. In addition to treatment and prevention, WO 2007/0880041 teaches that the compounds disclosed therein may include an in vivo imaging moiety and be used for in vivo imaging.

WO 2003/006491, WO 2005/012335 and WO 2005/123767 relate to RGD peptide-based compounds that bind to receptors associated with angiogenesis, said receptors including integrins. The compounds disclosed comprise either an anti-neoplastic agent or an in vivo imaging moiety and are taught as being useful in the treatment and in vivo imaging of diseases associated with angiogenesis.

WO 2006/054904 discloses use of RGD peptides labelled with an in vivo imaging moiety as contrast agents that target the extracellular matrix (ECM). The contrast agents are said to be useful in the diagnosis and monitoring of diseases related to the excessive formation of collagen, including liver fibrosis. However, there is a disincentive to using RGD peptides for in vivo imaging of liver fibrosis as it is known that excretion of radiolabelled integrin-binding RGD peptides occurs primarily via the hepatobiliary system (Haubner 1999 J. Nuc. Med.; 40: 1061-71). Additionally, as mentioned above, collagen is not an ideal marker for active fibrosis as it can be found when the disease process is resolving as well as in the latter stages of active disease. It would be more advantageous to target an earlier, active stage, when application of a treatment regimen is probably more appropriate, and also likely to be more clinically effective, e.g. the early stages of fibrosis in NASH, before liver cirrhosis develops. There is therefore a need for a method to identify the early states of liver fibrosis (also termed "fibrogenesis") and thereby intervene in the disease process at a stage where it can be most effectively treated.

SUMMARY OF THE INVENTION

The present invention relates to a method useful in facilitating the identification of fibrogenesis in the liver of a subject. The invention also provides a compound for use in a method for identification of fibrogenesis in the liver of a subject. A further aspect of the invention is a compound for use in the preparation of a medicament for use in a method for identification of fibrogenesis in the liver of a subject. The present invention demonstrates that RGD peptide-based compounds can be effectively used to detect activated hepatic stellate cells (HSCs), thereby providing a method useful in the early diagnosis of liver fibrosis.

DETAILED DESCRIPTION OF THE INVENTION

Figure 1:
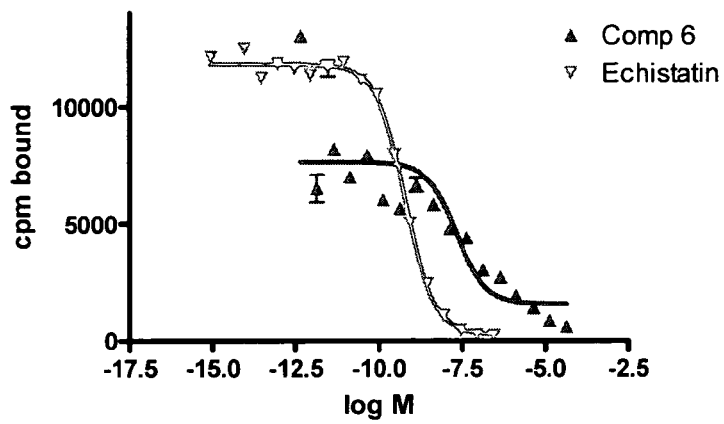
FIG. 1 and FIG. 2 show Compound 6 binding specifically to both activated human hepatic stellate cells and EA-Hy926 membranes. Ki was determined as ~10 nM in the EA-Hy926 membrane assay, and EC50 as ~1 nM in the LX-2 cell assay. Specificity of binding in the LX-2 assay was shown by virtue of the specific inhibition of Compound 6 binding by cold Compound 6. A low affinity scrambled negative control does not bind to integrins or activated stellate cells.

In one aspect, the present invention relates to a compound of Formula I for use in a method to determine of the presence, location and/or amount of fibrogenesis in the liver of a subject, said method comprising the following steps:
  (i) providing a subject to whom a detectable quantity of a compound of Formula I has been administered;
  (ii) allowing the compound of Formula I to bind to any fibrogenic tissue in said liver;
  (iii) detection of signals emitted by said compound of Formula I by an in vivo imaging method; and,
  (iv) generation of an image representative of the location and/or amount of said signals;
wherein said compound of Formula I is defined as follows:

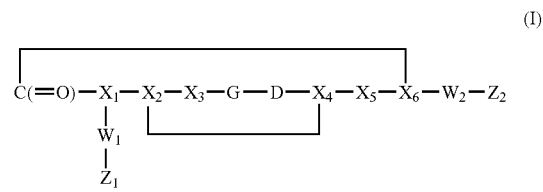

wherein:
G represents glycine;
D represents aspartic acid;
$X_1$ represents an amino acid selected from aspartic acid, glutamic acid, lysine, homolysine or a $C_{3-6}$ diaminoalkanoic acid, or derivatives thereof;
$X_2$ and $X_4$ independently represent amino acid residues whose side chains are linked together to form a cyclising bridge, such as cysteine or homocysteine forming disulphide or thioether bonds, or other amino acids capable of forming a cyclising bridge such as aspartic acid and lysine;
$X_3$ represents arginine, N-methylarginine or an arginine mimetic;
$X_5$ represents tyrosine, phenylalanine, 3-iodo-tyrosine $C_{4-6}$ cycloalkylalanine or naphthyl alanine, or derivatives thereof;
$X_6$, represents a thiol-containing amino acid that forms either a thioether bond or a thioacetal bond linking $X_6$ to the C(=O) group;
$W_1$ and $W_2$ are independently an optional linker moiety, wherein when present $W_1$ is linked to the amino acid side chain moiety of $X_1$ and $W_2$ when present is linked to the carboxy group of $X_6$; and,
$Z_1$ and $Z_2$ are independently an imaging moiety, a sugar moiety, and organic dye moiety or hydrogen, with the proviso that at least one of $Z_1$ and $Z_2$ is an imaging moiety.

For said compound of Formula I:
$X_1$ is preferably lysine.
$X_2$ and $X_4$ are preferably independently cysteine or homocysteine, and are most preferably both cysteine.
$X_3$ is preferably arginine.
$X_5$ is preferably cyclohexylalanine, phenylalanine or 3-iodo-tyrosine, and most preferably phenylalanine.
$X_6$, is preferably cysteine or homocysteine, and most preferably cysteine.

In a preferred embodiment of Formula I:
$X_1$ is lysine;
$X_2$ and $X_4$ are independently cysteine or homocysteine;
$X_3$ is arginine;
$X_5$ is phenylalanine or 3-iodo-tyrosine; and,
$X_6$ is cysteine or homocysteine.

In a most preferred embodiment of Formula I:
$X_1$ is lysine;
$X_2$ and $X_4$ are both cysteine;
$X_3$ is arginine;
$X_5$ is phenylalanine; and,
$X_6$ is cysteine.

In the present invention, the term "fibrogenesis" specifically relates to the active, progressive stage of fibrosis, when, amongst other things, hepatic stellate cells (HSC) are activated and express integrins. HSCs are widely regarded as the principal fibrocompetent cell in the liver. During fibrogenesis, HSC activate and proliferate, but during resolution of fibrosis there is extensive HSC apoptosis that coincides with degradation of the liver scar. Furthermore, during fibrogenesis, the deposition of extracellular matrix (ECM) components, such as collagen, has not yet taken place. The presence of ECM components is therefore characteristic of the later stages of fibrosis and of resolution of fibrosis. Targeting the disease process during fibrogenesis therefore provides a better indication of active disease where application of treatment is most appropriate.

In the present invention an "amino acid" consists of an amino group, a carboxyl group, a hydrogen atom, and an amino acid side chain moiety, all bonded (in the case of an alpha amino acid) to a single carbon atom that is referred to as an alpha carbon. Amino acids include, but are not limited to, naturally-occurring amino acids. Naturally-occurring amino acids are those from which the amino acid units of naturally-occurring proteins are derived, and are well-known to those skilled in the art of the present invention. The term "derivatives thereof" when used herein in connection with an amino acid means an amino acid wherein the side chain is a derivative of a naturally-occurring amino acid side chain (see "Amino Acid Derivatives" 1999 Oxford University Press, Barrett, Ed.).

By the term "amino acid mimetic" is meant synthetic analogues of naturally occurring amino acids which are isosteres, i.e. have been designed to mimic the steric and electronic structure of the natural compound. Such isosteres are well known to those skilled in the art and include but are not limited to depsipeptides, retro-inverso peptides, thioamides, cycloalkanes or 1,5-disubstituted tetrazoles (see M. Goodman, Biopolymers, 24, 137, (1985)).

The term "cyclising bridge" refers to any combination of amino acids, or amino acids and —$(CH_2)_o$— or —$(CH_2)_o$—$C_6H_4$-groups, with functional groups allowing for the introduction of a bridge (where o represents a positive integer from 1 to 10). Preferred examples are disulphides, disulphide mimetics such as the —$(CH_2)_4$-carba bridge, thioacetal, thioether bridges (cystathione or lanthionine), bridges containing esters and ethers, and amide bridges. Preferably, one bridge forms a disulphide bond and a second bridge comprises a thioether (sulphide) bond. When the cyclising bridge is formed by two amino acids, as with $X_2$ and $X_4$, for instance the side chain of one of cysteine or homocysteine is linked to the side chain of one of cysteine, homocysteine, serine, threonine, or an aldehyde-containing amino acid to form the cyclising bridge.

An "arginine mimetic" is a synthetic analogue of naturally occurring arginine which is an isostere, in the same way as defined above for amino acid mimetic.

The peptide part of the compound of Formula I can be synthesised using all known methods of chemical synthesis but particularly useful is the solid-phase methodology of Merrifield employing an automated peptide synthesiser (J. Am. Chem. Soc., 85:2149 (1964)). Standard procedures for the synthesis strategy are described in E. Atherton & R. C. Sheppard, "Solid Phase Peptide Synthesis: a Practical Approach", 1989, IRL Press, Oxford.

A synthesis resin with an acid-labile linker group, to which the desired protected C-terminal amino acid residue is attached by amide bond formation, is used. For example, a so-called Rink amide AM resin with a (dimethoxyphenyl-aminomethyl)-phenoxy-derived linker may be applied (Rink, H. (1987), Tetrahedron Lett. 30, p. 3787). Acidolytic cleavage of the peptide from this resin will yield a peptide amide. Alternatively, a O-Bis-(aminoetyl)ethylene glycol trityl resin (K. Barlos et al (1988), Liebigs Ann. Chem., p. 1079) can be used that upon acidolytic cleavage yields a peptide with a primary amine handle.

Labelling with an imaging moiety may be conveniently carried out by means of a "precursor compound", which is a derivative of said compound of Formula I, designed so that chemical reaction with a convenient chemical form of the desired imaging moiety/moieties occurs site-specifically; can be conducted in a minimal number of steps (ideally a single step); and without the need for significant purification (ideally no further purification), to give the desired compound of Formula I. Such precursor compounds are synthetic and can conveniently be obtained in good chemical purity. The precursor compound may optionally comprise one or more protecting groups for certain functional groups of Formula I.

By the term "protecting group" is meant a group which inhibits or suppresses undesirable chemical reactions, but which is designed to be sufficiently reactive that it may be cleaved from the functional group in question under mild enough conditions that do not modify the rest of the molecule. After deprotection the desired product is obtained. Protecting groups are well known to those skilled in the art and are suitably chosen from, for amine groups: Boc (where Boc is tert-butyloxycarbonyl), Fmoc (where Fmoc is fluorenylmethoxycarbonyl), trifluoroacetyl, allyloxycarbonyl, Dde [i.e. 1-(4,4-dimethyl-2,6-dioxocyclohexylidene)ethyl] or Npys (i.e. 3-nitro-2-pyridine sulfenyl); and for carboxyl groups: methyl ester, tert-butyl ester or benzyl ester. For hydroxyl groups, suitable protecting groups are: methyl, ethyl or tent-butyl; alkoxymethyl or alkoxyethyl; benzyl; acetyl; benzoyl; trityl (Trt) or trialkylsilyl such as tetrabutyldimethylsilyl. For thiol groups, suitable protecting groups are: trityl and 4-methoxybenzyl. The use of further protecting groups are described in 'Protective Groups in Organic Synthesis', Theorodora W. Greene and Peter G. M. Wuts, (Third Edition, John Wiley & Sons, 1999).

A "linker moiety" of the present invention is a radical of Formula -$(L)_n$- wherein:
each L is independently C(=O)—, —$CR'_2$—, —CR'=CR'—, —C≡C—, —$CR'_2CO_2$—, —$CO_2CR'_2$—, —NR'—, —NR'CO—, —CONR'—, —NR'(C=O)NR'—, —NR'(C=S)NR'—, —$SO_2NR'$—, —$NR'SO_2$—, —$CR'_2OCR'_2$—, —$CR'_2SCR'_2$—, —$CR'_2NR'CR'_2$—, a $C_{4-8}$ cycloheteroalkylene group, a $C_{4-8}$ cycloalkylene group, a $C_{5-12}$ arylene group, a $C_{3-12}$ heteroarylene group, an amino acid, a polyalkyleneglycol, polylactic acid or polyglycolic acid moiety;
n is an integer of value 1 to 15;
each R' group is independently H or $C_{1-10}$ alkyl, $C_{3-10}$ alkylaryl, $C_{2-10}$ alkoxyalkyl, $C_{1-10}$ hydroxyalkyl, $C_{1-10}$ fluoroalkyl, or 2 or more R' groups, together with the atoms to which they are attached form a carbocyclic, heterocyclic, saturated or unsaturated ring;
with the proviso that said linker moiety is a chain of no more than 100 atoms, preferably no more than 50 atoms. The linker moiety is most preferably a chain of between 10 and 50 atoms, and especially preferably a chain of between 10 and 30 atoms. Preferred L groups are —C(=O)—, —$CH_2$—, —NH—, —NHC(=O)—, —C(=O)NH—, —$CH_2$—O—$CH_2$—, and amino acids.

Preferably, the linker acts as a biomodifier moiety. A "biomodifier moiety" has the function of modifying the pharmacokinetics and blood clearance rates of the compound of Formula I. An example of a suitable biomodifier moiety is one based on a monodisperse PEG building block comprising 1 to 10 units of said building block. Additionally, said biomodifier moiety may also represent 1 to 10 amino acid residues. Preferred amino acid residues for said biomodifier moiety are charged amino acids such as lysine and glutamic acid, or charged non-natural amino acids such as cysteic acid and phosphonoalanine. In addition, the amino acids glycine, aspartic acid and serine may be included. In a preferred embodiment, the biomodifier moiety comprises a monodisperse PEG-like structure, the 17-amino-5-oxo-6-aza-3,9,12,15-tetraoxaheptadecanoic acid of Formula II:

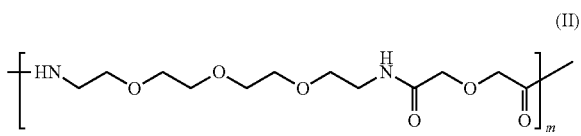

wherein m equals an integer from 1 to 10 and where the C-terminal unit is an amide moiety. The biomodifier moiety acts to modify the pharmacokinetics and blood clearance rates of the compounds. The function of the biomodifier moiety in the present invention is to decrease uptake in the tissues and increase excretion via the kidneys, thereby resulting in less background interference and giving a better in vivo image. The biomodifier moiety can further represent a moiety preferentially derived from glutaric and/or succinic acid and/or a polyethyleneglycol based unit and/or a unit of Formula II as illustrated above. The nature of the linker moiety should not interfere with the affinity of the compound of Formula I for its target receptors. In addition, the linker moiety should not act to increase the background liver uptake of the compound of Formula I, such as may occur if e.g. an overly-large polyethyleneglycol based unit were to be used.

Where either $Z_1$ or $Z_2$ is a sugar moiety it too may act as a biomodifier moiety. A "sugar moiety" is a carbohydrate group which is usually an aldehyde or a ketone derivative of a polyhydric alcohol. It may be a monomer (monosaccharide), such as fructose or glucose, or two sugars joined together to form a disaccharide. Disaccharides include sugars such as sucrose, which is made of glucose and fructose. The term sugar includes both substituted and non-substituted sugars, and derivatives of sugars. Preferably, the sugar is selected from glucose, glucosamine, galactose, galactosamine, mannose, lactose, fucose and derivatives thereof, such as sialic acid, a derivative of glucosamine. The sugar is preferably α or β. The sugar may especially be a manno- or galactose pyranoside. The hydroxyl groups on the sugar may be protected with, for example, one or more acetyl groups. The sugar moiety is preferably N-acetylated. Preferred examples of such sugars include N-acetyl galactosamine, sialic acid, neuraminic acid, N-acetyl galactose, and N-acetyl glucosamine.

The "organic dye moiety" can be any organic dye that interacts with light in the electromagnetic spectrum with wavelengths from the ultraviolet light to the near-infrared. Preferred organic dye moieties include groups having an extensive delocalized electron system. A most preferred organic dye moiety is a cyanine dye (CyDye™). Cyanine dyes are compounds defined by a polyene chain containing an odd number of carbon atoms linked by alternating single and multiple, preferably double, carbon-carbon bonds, terminated at either end by an amino group, one of which is quaternised. The cyanine and analogues aryl-linker-aryl chromophores optionally carry pendant or fused ring substituents. General description of cyanine dyes and synthesis thereof are described in U.S. Pat. No. 6,048,982, U.S. Pat. No. 5,268,486 and EP 1037947. Cyanine dyes for the present invention are preferably selected from the group consisting of carbacyanines, oxacyanines, thiacyanines and azacyanines.

The "detection" step of the method described herein involves the of signals emitted by the "imaging moiety" of Formula I by means of a detector sensitive to said signals. This detection step can also be understood as the acquisition of signal data. Examples of signals emitted by the imaging moiety that are suitable for use in the present invention are (i) any that may be detected externally to the human body, such as gamma rays; or, (ii) via use of detectors designed for use in vivo, such as radiation detectors designed for intra-operative use. The "generation" step of the method described herein is carried out by a computer which applies a reconstruction algorithm to the acquired signal data to yield a dataset. This dataset is then manipulated to generate images showing areas of interest within the subject.

The imaging moiety of the compound of the invention is preferably chosen from:
(i) a radioactive metal ion;
(ii) a gamma-emitting radioactive halogen;
(iii) a positron-emitting radioactive non-metal; and,
(iv) a paramagnetic metal ion.

When the imaging moiety is a radioactive metal ion, i.e. a radiometal, suitable radiometals can be either positron emitters such as $^{64}$Cu, $^{48}$V, $^{52}$Fe, $^{55}$Co, $^{94m}$Tc or $^{68}$Ga; or γ-emitters such as $^{99m}$Tc, $^{111}$In, $^{113m}$In, or $^{67}$Ga. Preferred radiometals are $^{99m}$Tc, $^{64}$Cu, $^{68}$Ga and $^{111}$In. Most preferred radiometals are γ-emitters, especially $^{99m}$Tc.

When the imaging moiety is a paramagnetic metal ion, suitable such metal ions include: Gd(III), Mn(II), Cu(II), Cr(III), Fe(III), Co(II), Ni(II), Eu(III) or Dy(III). Preferred paramagnetic metal ions are Gd(III), Mn(II) and Fe(III), with Gd(III) being especially preferred.

When the imaging moiety of the compound of Formula I is a metal ion, it is preferably present as a metal complex of the metal ion with a synthetic ligand. By the term "metal complex" is meant a coordination complex of the metal ion with one or more ligands. It is strongly preferred that the metal complex is "resistant to transchelation", i.e. does not readily undergo ligand exchange with other potentially competing ligands for the metal coordination sites. Potentially competing ligands include other excipients in the preparation in vitro (e.g. radioprotectants or antimicrobial preservatives used in the preparation), or endogenous compounds in vivo (e.g. glutathione, transferrin or plasma proteins). The term "synthetic" has its conventional meaning, i.e. man-made as opposed to being isolated from natural sources e.g. from the mammalian body. Such compounds have the advantage that their manufacture and impurity profile can be fully controlled.

Suitable ligands for use in the present invention which form metal complexes resistant to transchelation include: chelating agents, where 2-6, preferably 2-4, metal donor atoms are arranged such that 5- or 6-membered chelate rings result (by having a non-coordinating, backbone of either carbon atoms or non-coordinating heteroatoms linking the metal donor atoms); or monodentate ligands which comprise donor atoms which bind strongly to the metal ion, such as isonitriles, phosphines or diazenides. Examples of donor atom types which bind well to metals as part of chelating agents are: amines, thiols, amides, oximes, and phosphines. Phosphines form such strong metal complexes that even monodentate or bidentate phosphines form suitable metal complexes. The linear geometry of isonitriles and diazenides is such that they do not lend themselves readily to incorporation into chelating agents, and are hence typically used as monodentate ligands.

Examples of suitable isonitriles include simple alkyl isonitriles such as tert-butylisonitrile, and ether-substituted isonitriles such as MIBI (i.e. 1-isocyano-2-methoxy-2-methylpropane). Examples of suitable phosphines include Tetrofosmin, and monodentate phosphines such as tris(3-methoxypropyl) phosphine. Examples of suitable diazenides include the HYNIC series of ligands i.e. hydrazine-substituted pyridines or nicotinamides.

When the metal ion is technetium, suitable chelating agents which form metal complexes resistant to transchelation include, but are not limited to:
(i) diaminedioximes;
(ii) $N_3S$ ligands having a thioltriamide donor set such as $MAG_3$ (mercaptoacetyltriglycine) and related ligands; or having a diamidepyridinethiol donor set such as Pica;
(iii) $N_2S_2$ ligands having a diaminedithiol donor set such as BAT or ECD (i.e. ethylcysteinate dimer), or an amideaminedithiol donor set such as MAMA;
(iv) $N_4$ ligands which are open chain or macrocyclic ligands having a tetramine, amidetriamine or diamidediamine donor set, such as cyclam, monoxocyclam dioxocyclam; and,
(v) $N_2O_2$ ligands having a diaminediphenol donor set.

Preferred chelating agents of the invention when the imaging moiety is technetium are diaminedioximes and tetraamines, preferred versions of which are now described in more detail.

Preferred diaminedioximes are of Formula VII:

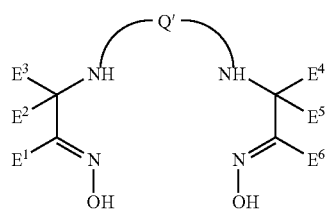

(VII)

where $E^1$-$E^6$ are each independently an R* group;
each R* is H or $C_{1-10}$ alkyl, $C_{3-10}$ alkylaryl, $C_{2-10}$ alkoxyalkyl, $C_{1-10}$ hydroxyalkyl, $C_{1-10}$ fluoroalkyl, $C_{2-10}$ carboxyalkyl or $C_{1-10}$ aminoalkyl, or two or more R* groups together with the atoms to which they are attached form a carbocyclic, heterocyclic, saturated or unsaturated ring, and wherein one or more of the R* groups is conjugated to the CBP;
and Q' is a bridging group of formula -(J')$_e$-;
where e is 3, 4 or 5 and each J' is independently —O—, —NR*— or —C(R*)$_2$— provided that -(J')$_e$- contains a maximum of one J' group which is —O— or NR*—.

Preferred Q' groups are as follows:
Q'=—(CH$_2$)(CHR*)(CH$_2$)— i.e. propyleneimine oxime or PnAO derivatives;
Q'=—(CH$_2$)$_2$(CHR*)(CH$_2$)$_2$— i.e. pentyleneamine oxime or PentAO derivatives;
Q'=—(CH$_2$)$_2$NR*(CH$_2$)$_2$—.

$E^1$ to $E^6$ are preferably chosen from: $C_{1-3}$ alkyl, alkylaryl alkoxyalkyl, hydroxyalkyl, fluoroalkyl, carboxyalkyl or aminoalkyl. Most preferably, each $E^1$ to $E^6$ group is $CH_3$.

The diaminedioxime is preferably conjugated at either the $E^1$ or $E^6$R* group, or an R* group of the Q' moiety. Most preferably, it is conjugated at an R* group of the Q' moiety. When it is conjugated at an R* group of the Q' moiety, the R* group is preferably at the bridgehead position. In that case, Q' is preferably —(CH$_2$)(CHR*)(CH$_2$)—, (CH$_2$)$_2$(CHR*) (CH$_2$)$_2$— or —(CH$_2$)$_2$NR*(CH$_2$)$_2$—, most preferably —(CH$_2$)$_2$(CHR*)(CH$_2$)$_2$—. An especially preferred diaminedioxime has the Formula VIIa:

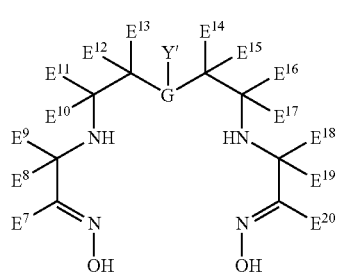

(VIIa)

where:
$E^7$-$E^{20}$ are each independently an R* group as defined above;
G is N or CR*; and
Y' is the point of attachment to the peptide portion of Formula I.

A preferred chelator of Formula VIIa is of Formula VIIb:

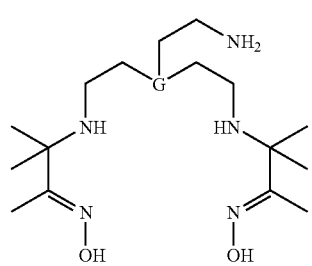

(VIIb)

where G is as defined above, and is preferably CH. A method for the preparation of Chelate I is disclosed in WO 03/006070.

Preferred tetraamine chelators are of Formula VIII:

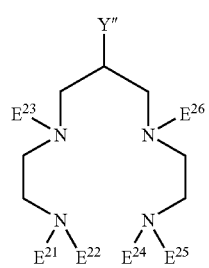

(VIII)

wherein:
Y" is the point of attachment to the rest of Formula I; and,
$E^{21}$ to $E^{26}$ are R* groups as previously defined.

A most preferred tetraamine chelate is of Formula VIIa:

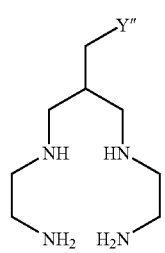

(VIIIa)

wherein Y" is as defined above. A method for the synthesis of a chelate of Formula VIIIa is disclosed in WO 06/008496.

The above described ligands are particularly suitable for complexing technetium e.g. $^{94m}$Tc or $^{99m}$Tc, and are described more fully by Jurisson et al (Chem. Rev., 99, 2205-2218 (1999)). The ligands are also useful for other metals, such as copper ($^{64}$Cu or $^{67}$Cu), vanadium (e.g. $^{48}$V), iron (e.g. $^{52}$Fe), or cobalt (e.g. $^{55}$Co).

Other suitable ligands are described in Sandoz WO 91/01144, which includes ligands which are particularly suitable for indium, yttrium and gadolinium, especially macrocyclic aminocarboxylate and aminophosphonic acid ligands. Ligands which form non-ionic (i.e. neutral) metal complexes of gadolinium are known and are described in U.S. Pat. No. 4,885,363. Particularly preferred for gadolinium are chelates including DTPA, ethylene diamine tetraacetic acid (EDTA), triethylene tetraamine hexaacetic acid (TTHA), 1,4,7,10-tetraazacyclododecane-1,4,7,10-tetraacetic acid (DOTA), 10-(2-hydroxypropyl)-1,4,7,10-tetraazacyclododecane-1,4,7-triacetic acid (DO3A) and derivatives of these.

When the imaging moiety is a metal ion present as part of a metal complex, an associated linker moiety is preferably present. The role of the linker moiety in this case is to distance the relatively bulky metal complex, which results upon metal coordination, from the active site of the peptide so that e.g. substrate binding is not impaired. This can be achieved by a combination of flexibility (e.g. simple alkyl chains), so that the bulky group has the freedom to position itself away from the active site and/or rigidity such as a cycloalkyl or aryl spacer which orientates the metal complex away from the active site. Preferred linker moieties in the context of these chelators have a backbone chain which contains 2 to 10 atoms, most preferably 2 to 5 atoms, with 2 or 3 atoms being especially preferred. A minimum linker group backbone chain of 2 atoms confers the advantage that the chelator is well-separated from the peptide so that any interaction is minimised. Furthermore, the peptide is unlikely to compete effectively with the coordination of the chelator to the metal ion. In this way, both the biological targeting characteristics of the peptide, and the metal complexing capability of the chelator are maintained. It is strongly preferred that the metal complex is bound to the peptide in such a way that the linkage does not undergo facile metabolism in blood. That is because such metabolism would result in the imaging metal complex being cleaved off before the labelled peptide reaches the desired in vivo target site. The peptide is therefore preferably covalently bound to the metal complex via linker moieties comprising linkages which are not readily metabolised. Suitable such linkages are carbon-carbon bonds, amide bonds, urea or thiourea linkages, or ether bonds.

Non-peptide linker groups such as alkylene groups or arylene groups have the advantage that there is no significant hydrogen bonding with the peptide part of Formula I so that the linker does not interact with the peptide. Preferred alkylene spacer groups are —(CH$_2$)$_q$— where q is an integer of value 2 to 5. Preferably q is 2 or 3. Preferred arylene spacers are of Formula IX:

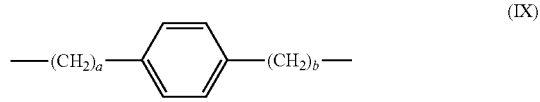

(IX)

where: a and b are each independently 0, 1 or 2.

A preferred linker moiety here is thus —CH$_2$CH$_2$-(L)$_p$- where L is as defined above and p is an integer of value 0 to 3. Most preferably, -(L)$_p$- is —CO— or —NR—. For Formula VIIb, when G is N and -(L)$_p$- is —NH—, this grouping has the additional advantage that it stems from the symmetrical intermediate N(CH$_2$CH$_2$NH$_2$)$_3$, which is commercially available.

When the imaging metal is technetium, the usual technetium starting material is pertechnetate, i.e. TcO$_4^-$ which is technetium in the Tc(VII) oxidation state. Pertechnetate itself does not readily form metal complexes, hence the preparation of technetium complexes usually requires the addition of a suitable reducing agent such as stannous ion to facilitate complexation by reducing the oxidation state of the technetium to the lower oxidation states, usually Tc(I) to Tc(V). The solvent may be organic or aqueous, or mixtures thereof. When the solvent comprises an organic solvent, the organic solvent is preferably a biocompatible solvent, such as ethanol or DMSO. Preferably the solvent is aqueous, and is most preferably isotonic saline.

When the imaging moiety is a gamma-emitting radioactive halogen, the radiohalogen is suitably chosen from $^{123}$I, $^{131}$I or $^{77}$Br. $^{125}$I is specifically excluded as it is not suitable for use as an imaging moiety for external in vivo imaging. A preferred gamma-emitting radioactive halogen for in vivo imaging is $^{123}$I.

Where the imaging moiety is radioiodine, the compound of Formula I can be obtained by means of a precursor compound comprising a derivative which either undergoes electrophilic or nucleophilic iodination or undergoes condensation with a labelled aldehyde or ketone. Examples of the first category are:

(a) organometallic derivatives such as a trialkylstannane (e.g. trimethylstannyl or tributylstannyl), or a trialkylsilane (e.g. trimethylsilyl) or an organoboron compound (e.g. boronate esters or organotrifluoroborates):

(b) a non-radioactive alkyl bromide for halogen exchange or alkyl tosylate, mesylate or triflate for nucleophilic iodination;

(c) aromatic rings activated towards nucleophilic iodination (e.g. aryl iodonium salt aryl diazonium, aryl trialkylammonium salts or nitroaryl derivatives).

Preferred such precursor compounds comprise: a non-radioactive halogen atom such as an aryl iodide or bromide (to permit radioiodine exchange); an organometallic precursor compound (e.g. trialkyltin, trialkylsilyl or organoboron compound); or an organic precursor such as triazenes or a good leaving group for nucleophilic substitution such as an iodonium salt. Preferably for radioiodination, the precursor compound comprises an organometallic precursor compound, most preferably trialkyltin.

Precursor compounds and methods of introducing radioiodine into organic molecules are described by Bolton (J. Lab. Comp. Radiopharm., 45, 485-528 (2002)). Suitable boronate ester organoboron compounds and their preparation are described by Kabalka et al (Nucl. Med. Biol., 29, 841-843 (2002) and 30, 369-373 (2003)). Suitable organotrifluoroborates and their preparation are described by Kabalka et al (Nucl. Med. Biol., 31, 935-938 (2004)).

Examples of aryl groups to which radioactive iodine can be attached are given below:

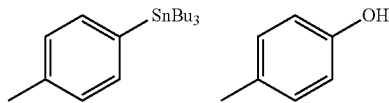

Both contain substituents which permit facile radioiodine substitution onto the aromatic ring. A tyrosine residue permits radioiodination to be carried out using its inherent phenol group.

Alternative substituents containing radioactive iodine can be synthesised by direct iodination via radiohalogen exchange, e.g.

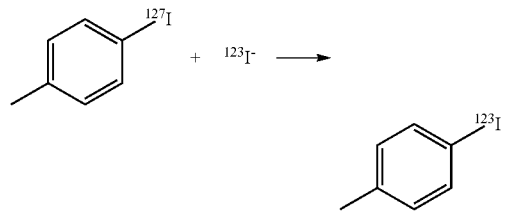

The radioiodine atom is preferably attached via a direct covalent bond to an aromatic ring such as a benzene ring, or a vinyl group since it is known that iodine atoms bound to saturated aliphatic systems are prone to in vivo metabolism and hence loss of the radioiodine.

When the imaging moiety is a positron-emitting radioactive non-metal, suitable such positron emitters include: $^{11}$C, $^{13}$N, $^{15}$O, $^{17}$F, $^{18}$F, $^{75}$Br, $^{76}$Br or $^{124}$I. Preferred positron-emitting radioactive non-metals are $^{11}$C, $^{13}$N, $^{18}$F and $^{124}$I, especially $^{11}$C and $^{18}$F, most especially $^{18}$F.

Radiofluorination may be carried out via direct labelling using the reaction of $^{18}$F-fluoride with a suitable chemical group in a precursor compound having a good leaving group, such as an alkyl bromide, alkyl mesylate or alkyl tosylate. $^{18}$F can also be introduced by alkylation of N-haloacetyl groups with a $^{18}$F(CH$_2$)$_3$OH reactant, to give —NH(CO)CH$_2$O(CH$_2$)$_3$$^{18}$F derivatives. For aryl systems, $^{18}$F-fluoride nucleophilic displacement from an aryl diazonium salt, aryl nitro compound or an aryl quaternary ammonium salt are suitable routes to aryl-$^{18}$F derivatives.

A $^{18}$F-labelled compound of the invention may be obtained by formation of $^{18}$F fluorodialkylamines and subsequent amide formation when the $^{18}$F fluorodialkylamine is reacted with a precursor containing, e.g. chlorine, P(O)Ph$_3$ or an activated ester.

A further approach for radiofluorination, which is particularly suitable for radiofluorination of peptides, is described in WO 03/080544 and uses thiol coupling. A precursor compound comprising of one of the following substituents:

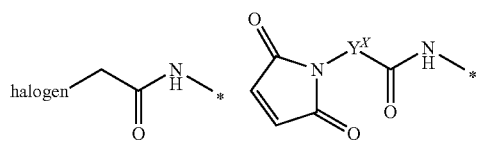

is reacted with a compound of Formula X:

  (X)

wherein Y$^X$ is a linker moiety of formula -(L$^Y$)$_y$- wherein L$^Y$ is as previously defined for L, y is 1-10 and optionally includes 1-6 heteroatoms;

X$^X$ is a linker of formula -(L$^X$)$_x$- wherein L$^X$ is as previously defined for L, x is 1-30 and optionally includes 1 to 10 heteroatoms; and,

* defines the point of attachment to the rest of the compound;

to give radiofluorinated imaging agents of formula (Xa) or (Xb) respectively:

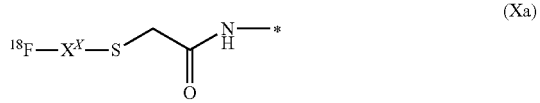  (Xa)

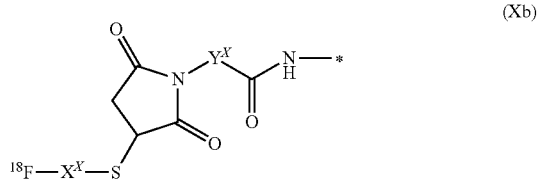  (Xb)

wherein X$^X$, Y$^X$, and * are as defined above.

An additional approach particularly suitable for radiofluorination of peptides is described in WO 04/080492 and makes use of aminoxy coupling. Radiofluorination is carried out by reaction of a precursor compound of formula (XI) with a compound of formula (XIa):

  (XI)

  (XIa)

or, by reaction of a precursor compound of formula (XII) with a compound of formula (XIIa):

  (XII)

  (XIIa)

wherein;

X$^{XI}$ and X$^{XII}$ are linker groups -(L$^{XI}$)$_z$- wherein L$^{XI}$ is as previously defined for L, z is 1-10 and optionally includes 1-6 heteroatoms;

R$^1$ is an aldehyde moiety, a ketone moiety, a protected aldehyde such as an acetal, a protected ketone, such as a ketal, or a functionality, such as diol or N-terminal serine residue, which can be rapidly and efficiently oxidised to an aldehyde or ketone using an oxidising agent;

R$^2$ is a functional group which, under mild conditions such as aqueous buffer, reacts site-specifically with R$^1$ yielding a stable conjugate. R$^2$ can be ammonia derivatives such as primary amine, secondary amine, hydroxylamine, hydrazine, hydrazide, aminoxy, phenylhydrazine, semicarbazide, or thiosemicarbazide, and is preferably a hydrazine, hydrazide or aminoxy group;

R$^3$ is a functional group which reacts site-specifically with R$^4$. R$^3$ can be ammonia derivatives such as primary amine, secondary amine, hydroxylamine, hydrazine, hydrazide, aminoxy, phenylhydrazine, semicarbazide, or thiosemicarbazide, and is preferably a hydrazine, hydrazide or aminoxy group;

R$^4$ is an aldehyde moiety, a ketone moiety, a protected aldehyde such as an acetal, a protected ketone, such as a ketal, or a functionality, such as diol or N-terminal serine residue, which can be rapidly and efficiently oxidised to an aldehyde or ketone using an oxidising agent;

to give a conjugate of formula (XIII) or (XIV), respectively:

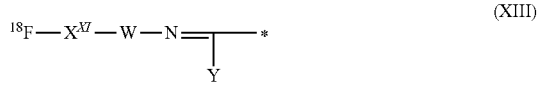  (XIII)

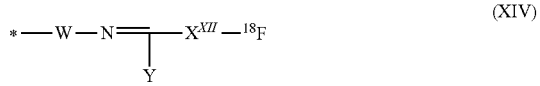  (XIV)

wherein W is —CO—NH—, —NH—, —O—, —NH-CONH—, or —NHCSNH—, and is preferably —CO—NH—, —NH— or —O—Y is H, $C_{1-6}$ alkyl or $C_{5-6}$ aryl substituents, and wherein $X^{XI}$, $X^{XII}$ and * are as previously defined.

Further details of synthetic routes to $^{18}F$-labelled derivatives are described by Bolton, J. Lab. Comp. Radiopharm., 45, 485-528 (2002).

Preferred imaging moieties are those which can be detected externally in a non-invasive manner following administration in vivo, such as by means of single photon emission tomography (SPECT), positron emission tomography (PET) and magnetic resonance imaging (MRI). Most preferred imaging moieties are radioactive, especially radioactive metal ions, gamma-emitting radioactive halogens and positron-emitting radioactive non-metals, particularly those suitable for imaging using SPECT or PET, e.g. $^{99m}Tc$, $^{123}I$, $^{11}C$ and $^{18}F$.

In one preferred embodiment, $W_1$ and $W_2$ both represent linker moieties, $Z_1$ represents an organic dye moiety, and $Z_2$ represents an imaging moiety. These compounds and methods for their preparation are presented in WO 2006/054904. Most preferably, $Z_2$ is a radioactive imaging moiety. Examples of these preferred compounds include the following:

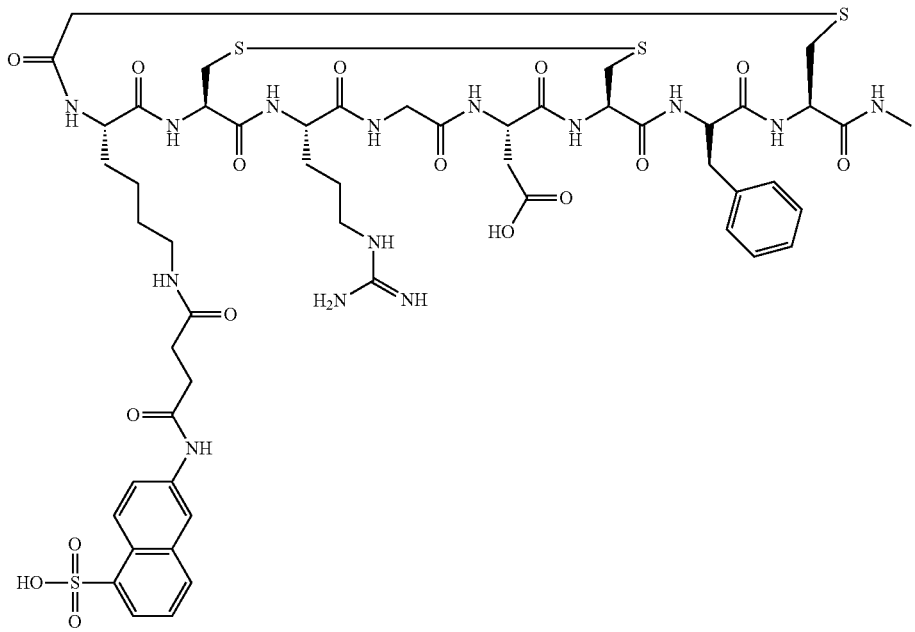

Compound 1

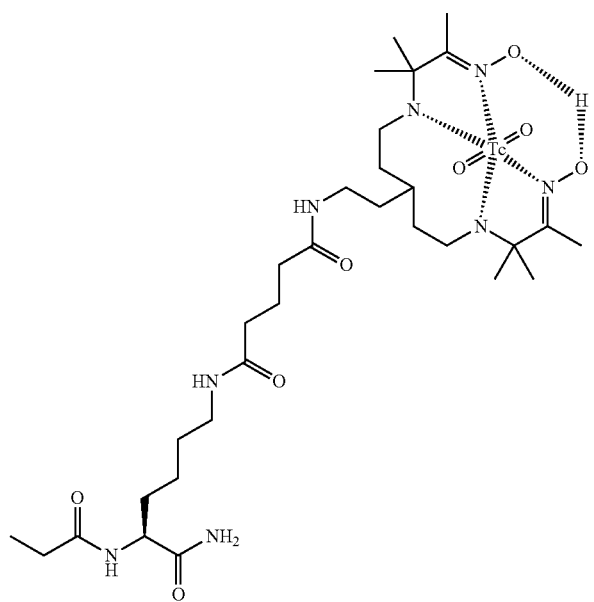

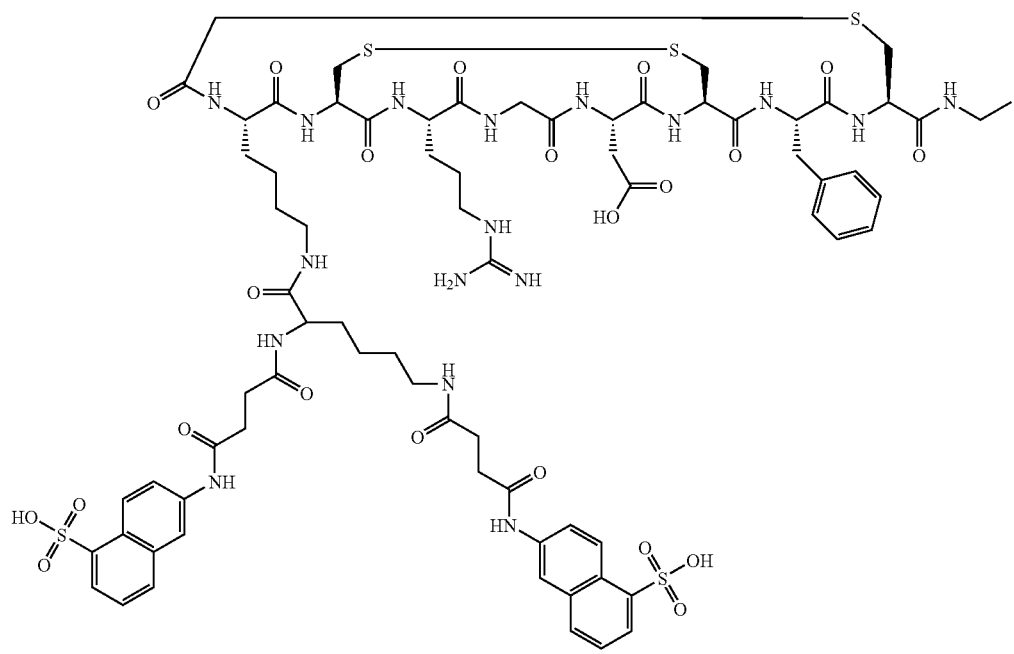
Compound 2
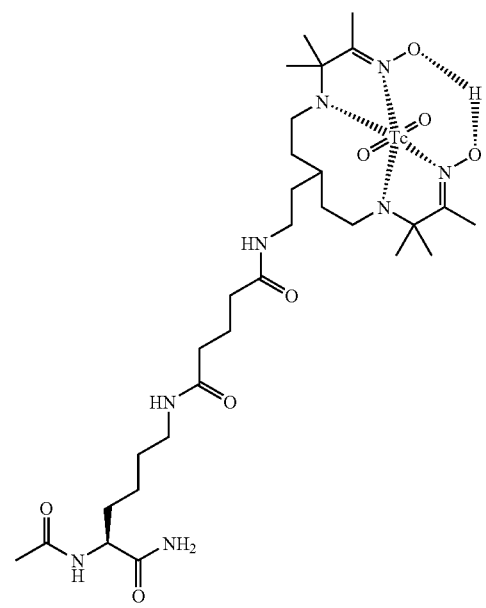

-continued
Compound 3
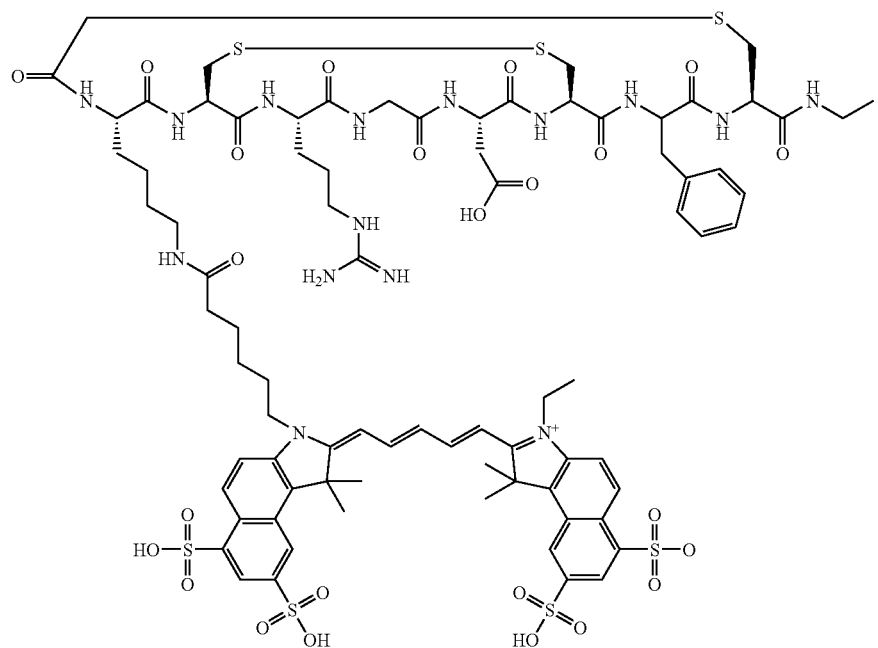
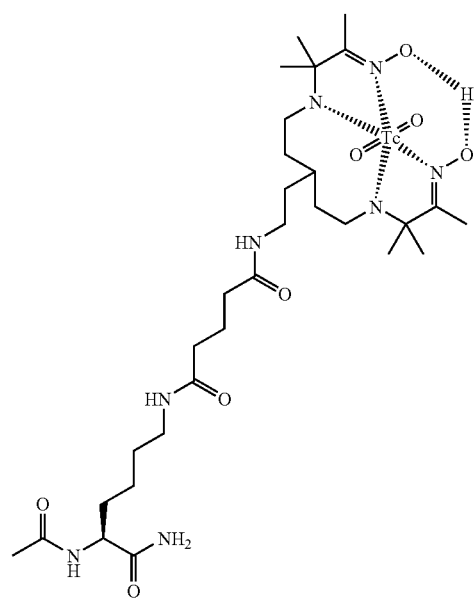

-continued

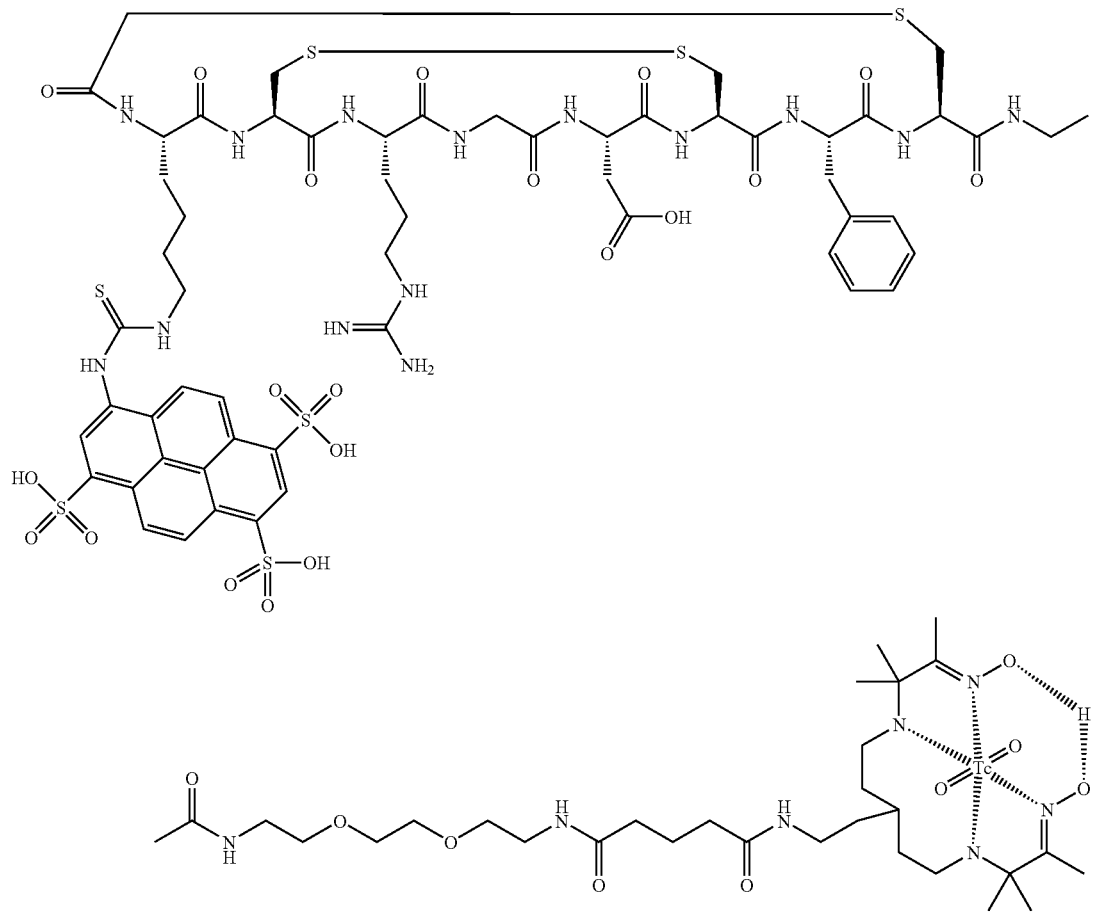

Compound 4

Methods for the preparation of Compounds 1 to 4 are detailed in WO 2006/054904.

In an alternative preferred embodiment, $W_1$ represents a linker moiety, $Z_1$ represents an imaging moiety, $W_2$ represents an optional linker moiety, and $Z_2$ is hydrogen. These compounds and methods for their preparation are presented in WO 2005/012335. Examples of these preferred compounds include the following:

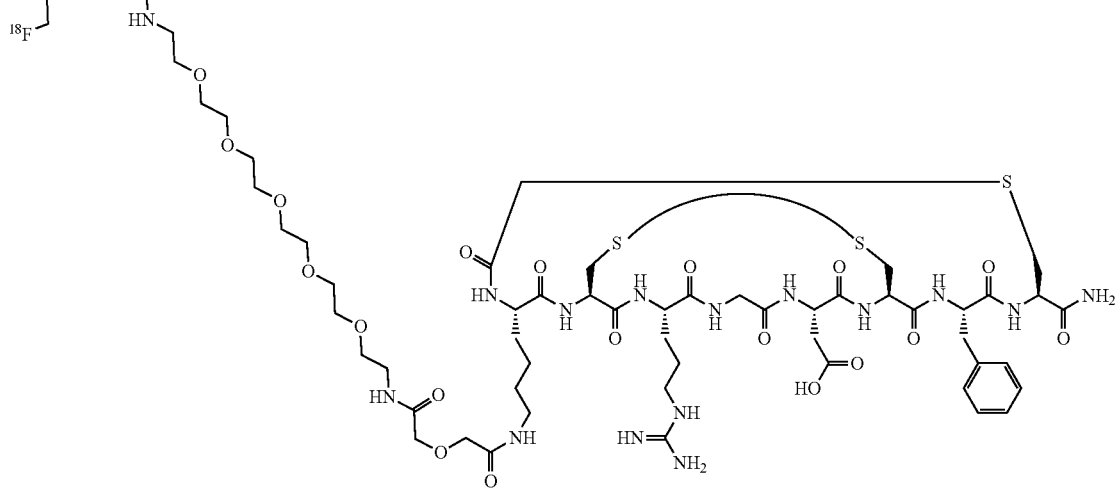

Compound 5

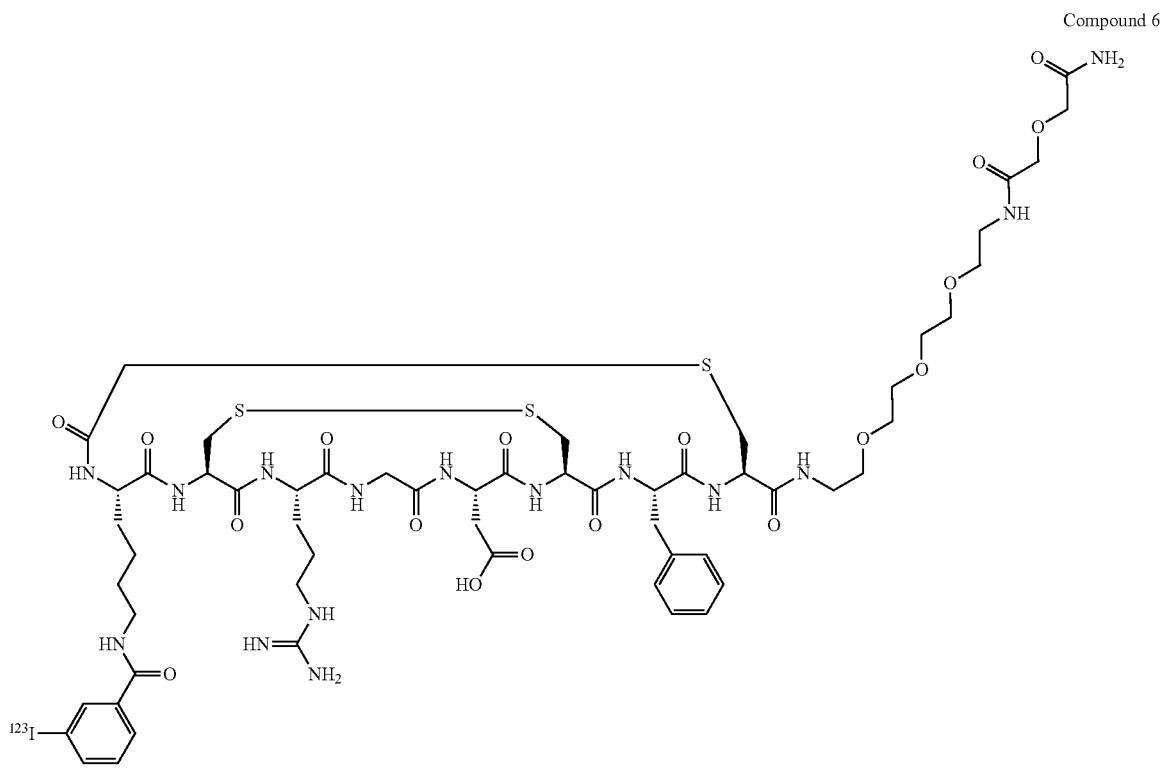

Compound 6

Methods for the preparation of Compounds 5 and 6 are detailed in WO 2005/012335

In a yet further alternative preferred embodiment, $W_1$ represents an optional linker moiety, $Z_1$ is hydrogen, $W_2$ represents a linker moiety, and $Z_2$ represents an imaging moiety. These compounds and methods for their preparation are presented in WO 2003/006491. Examples of these preferred compounds include the following:

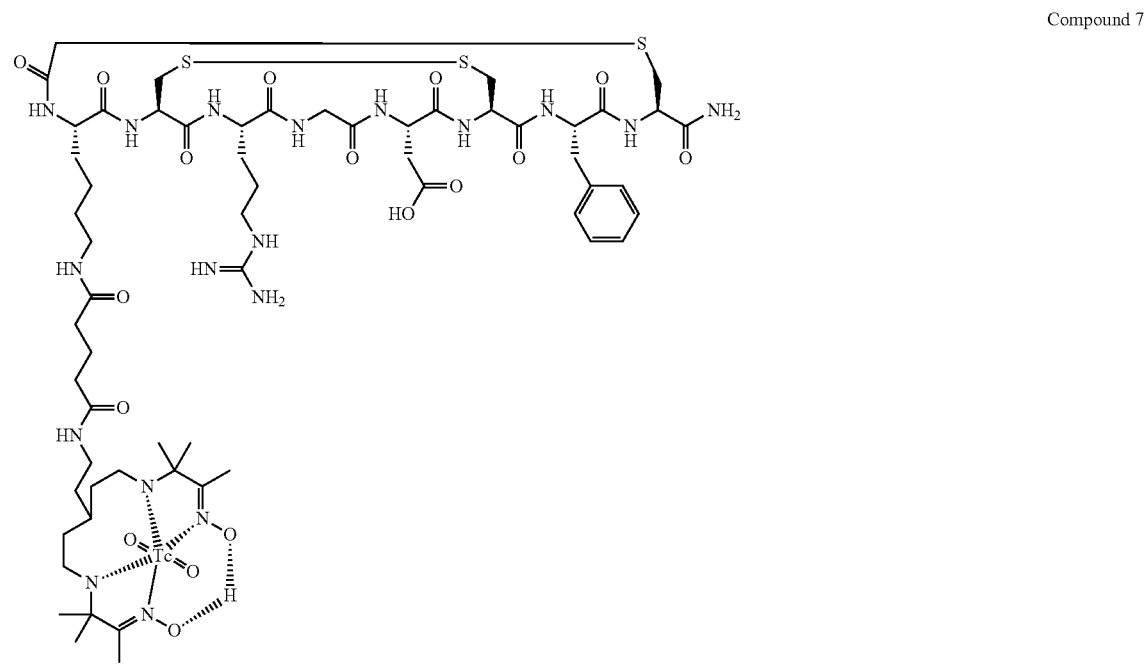

Compound 7

-continued
Compound 8
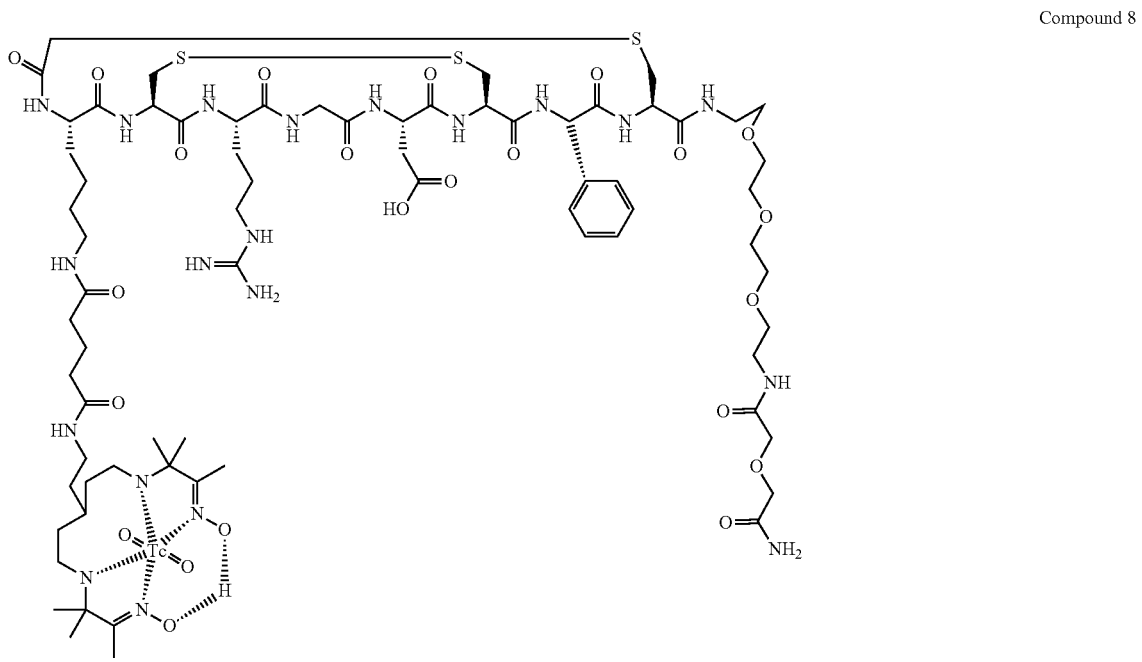
Compound 9
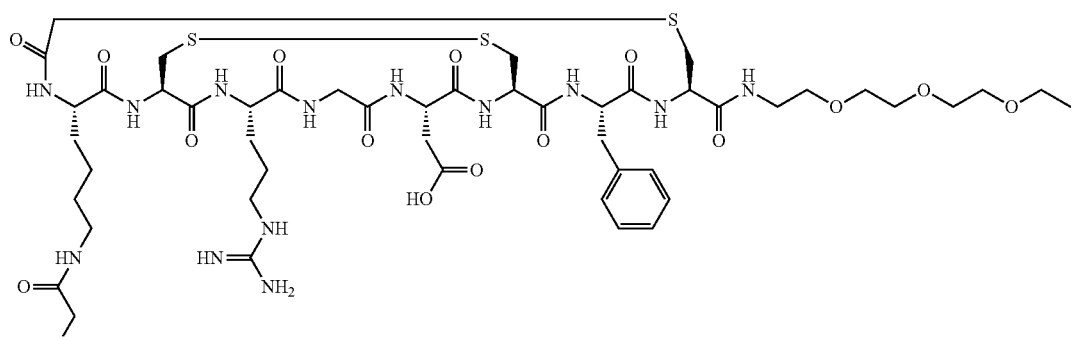
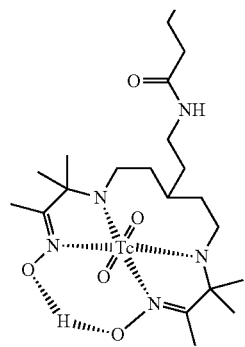

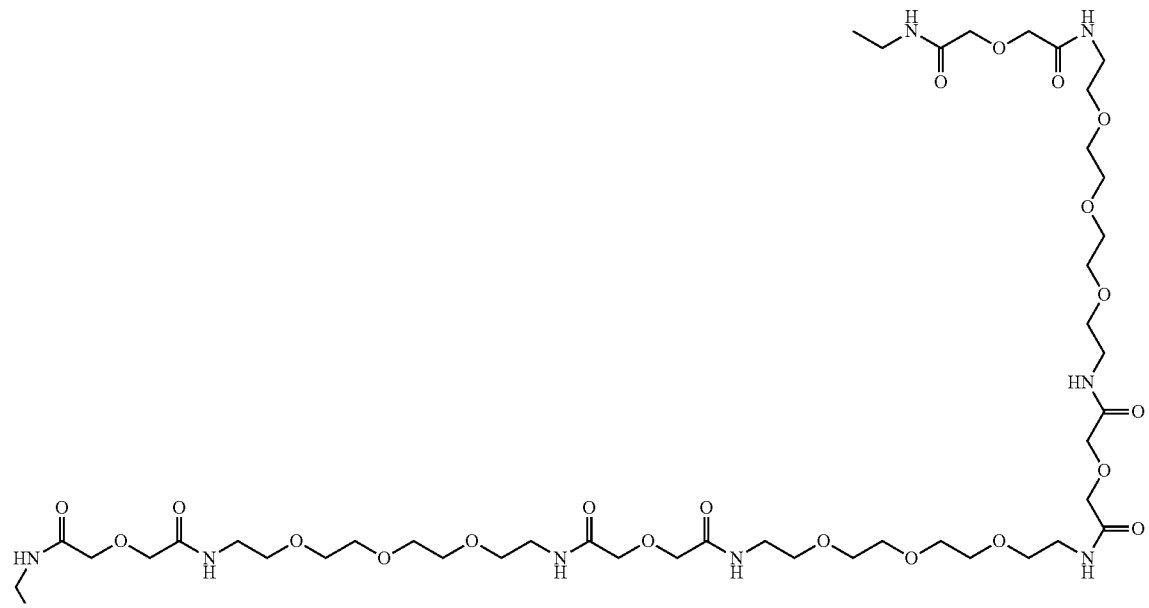
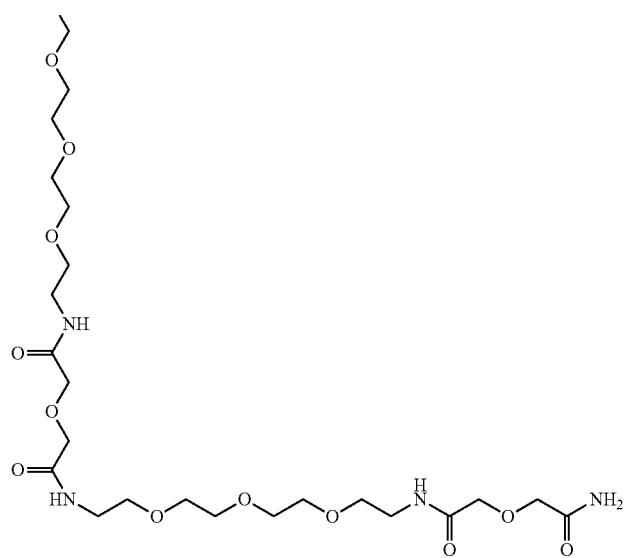

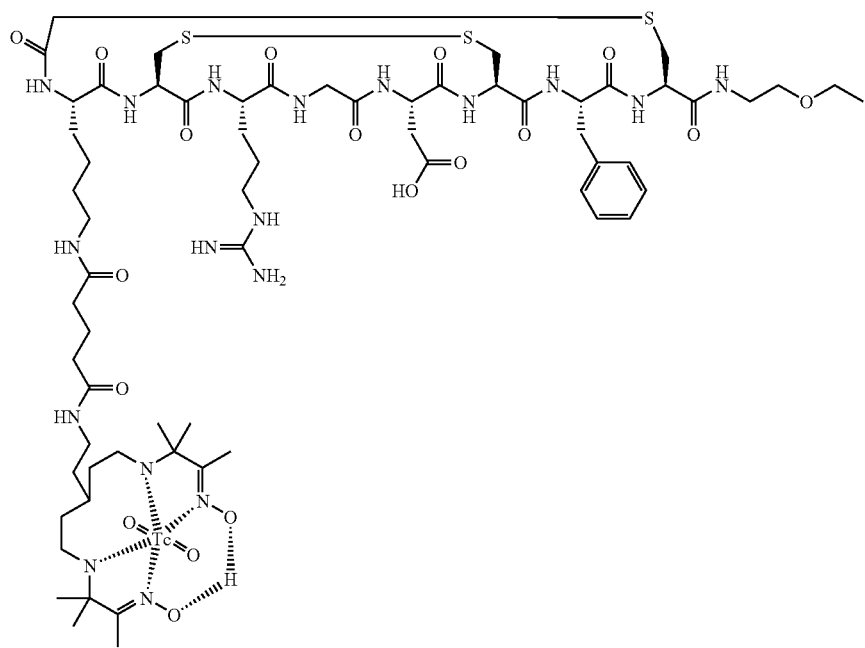
Compound 10
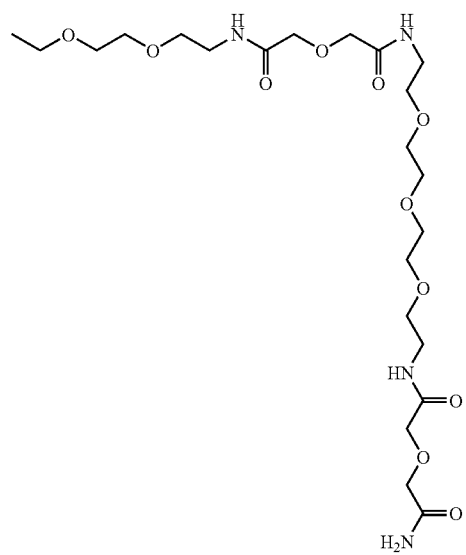

Methods for the preparation of Compounds 7 to 10 are detailed in WO 2003/006491.
For Compounds 1 to 4 and 7 to 10, it is furthermore alternatively preferred that the diamine dioxime chelate moiety is replaced with a tetraamine chelate moiety to form Compounds 1a to 4a and 7a to 10a:
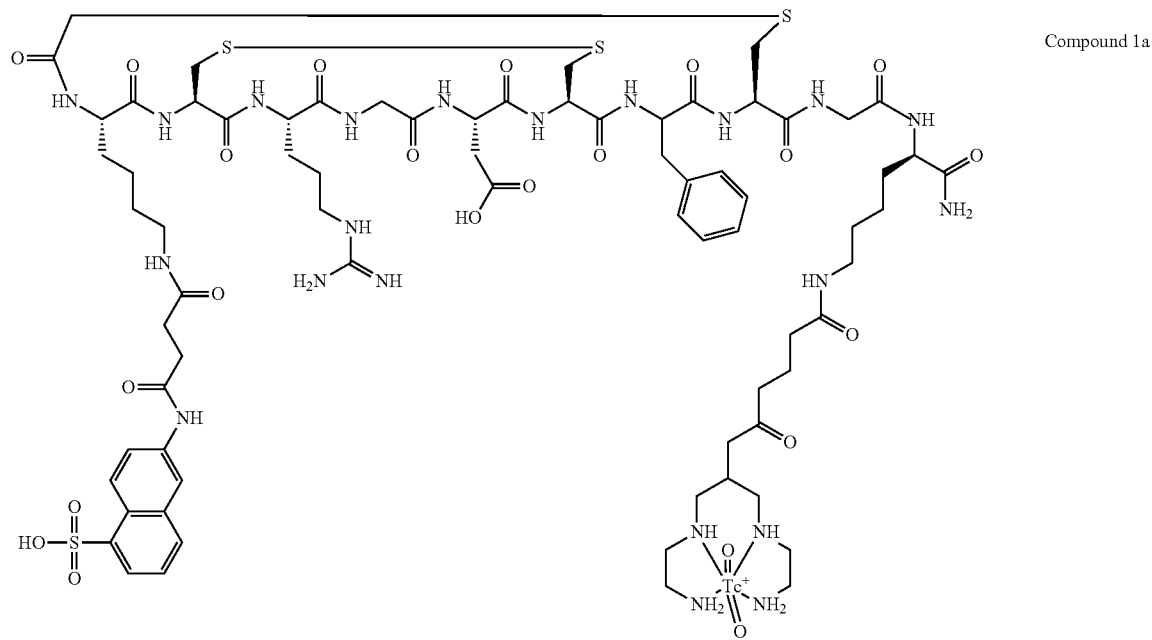
Compound 1a
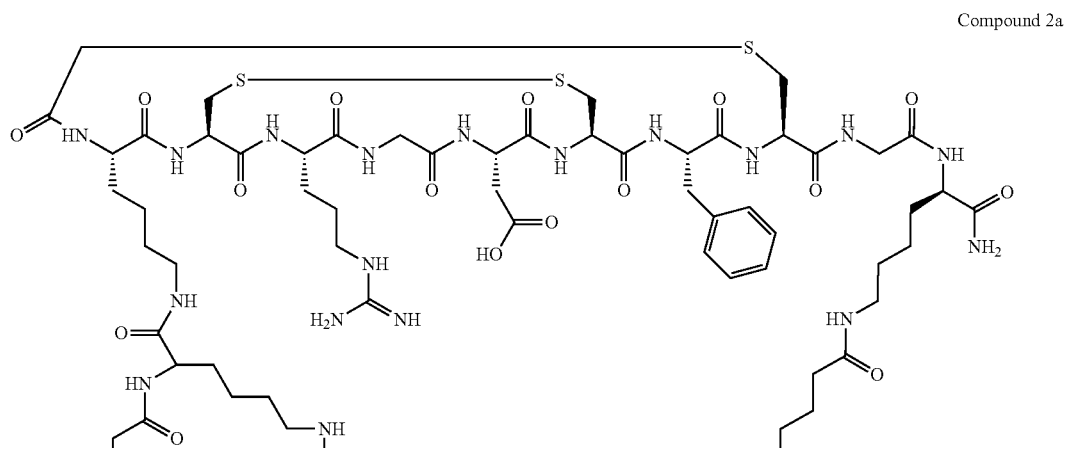
Compound 2a
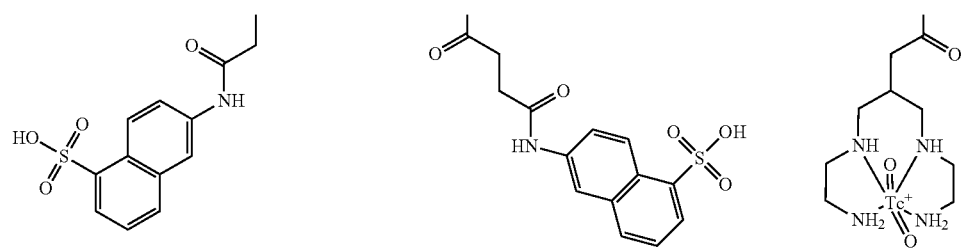

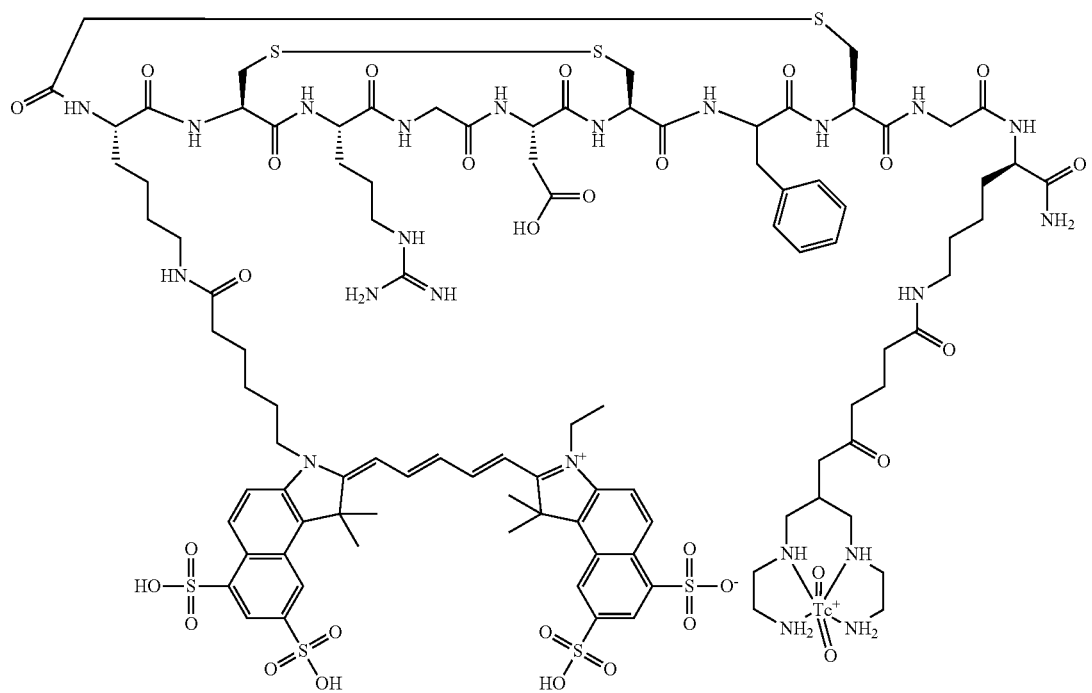
Compound 3a
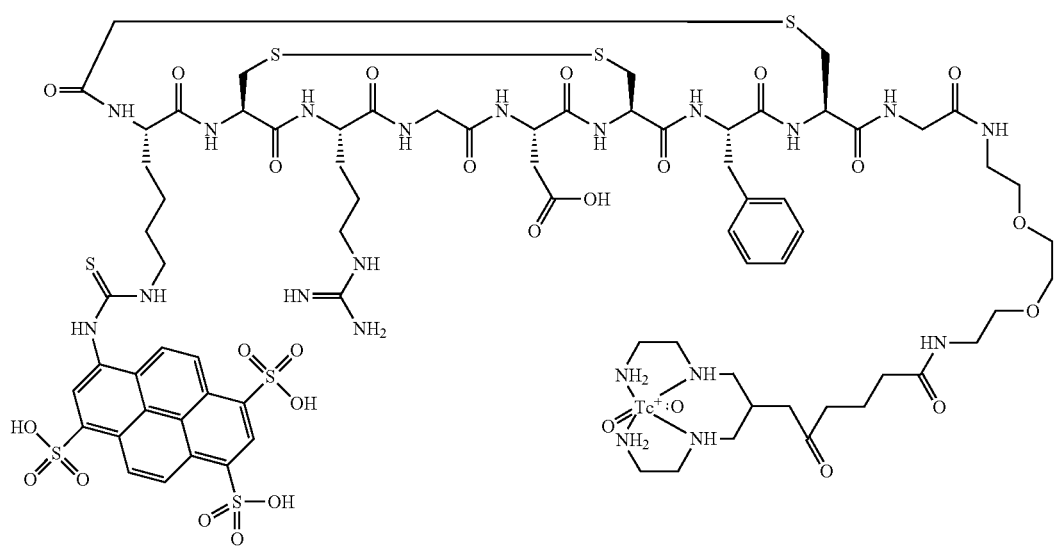
Compound 4a

-continued
Compound 7a
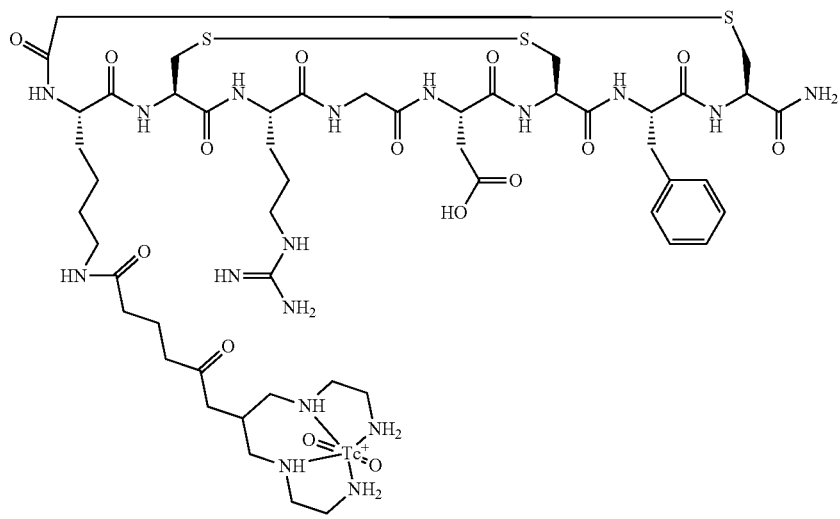
Compound 8a
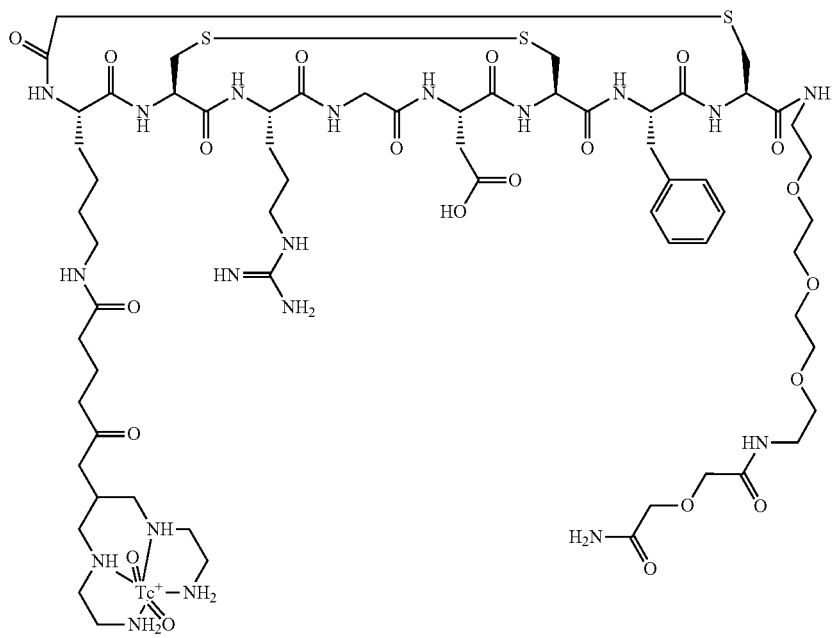
Compound 9a
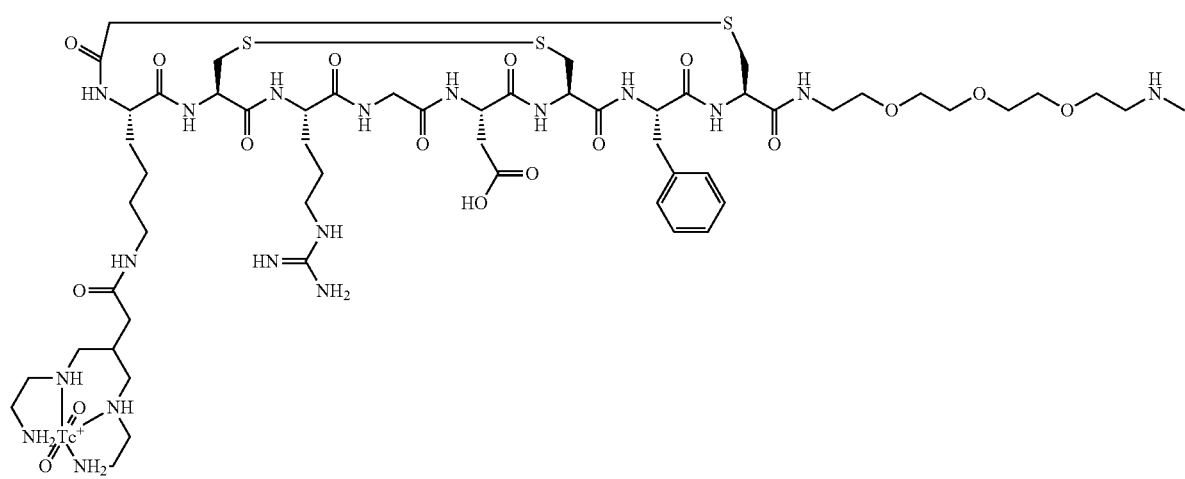

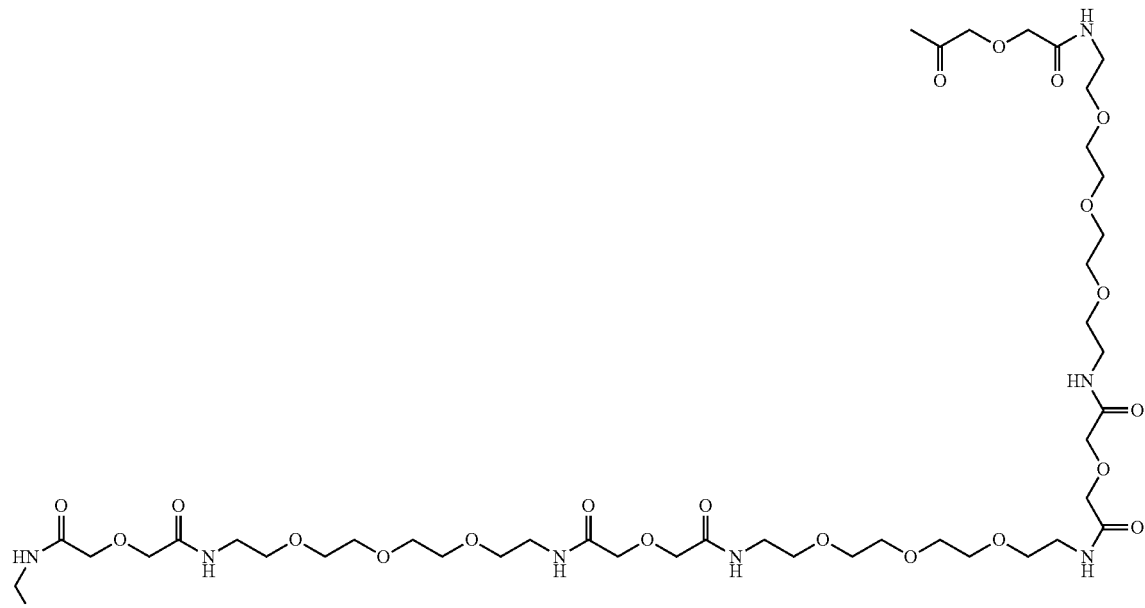
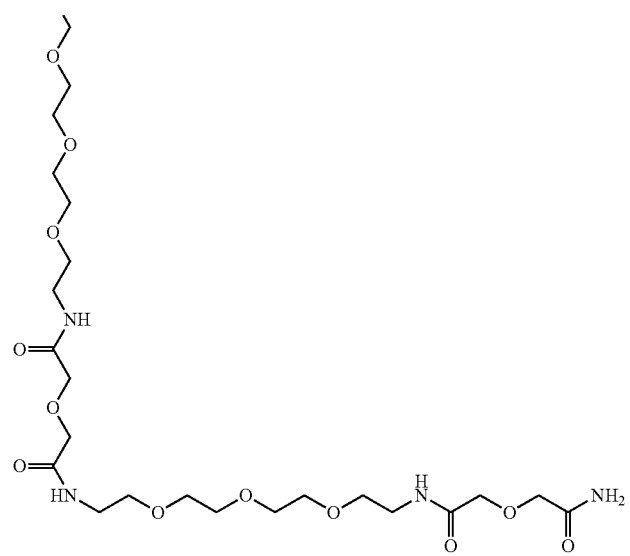

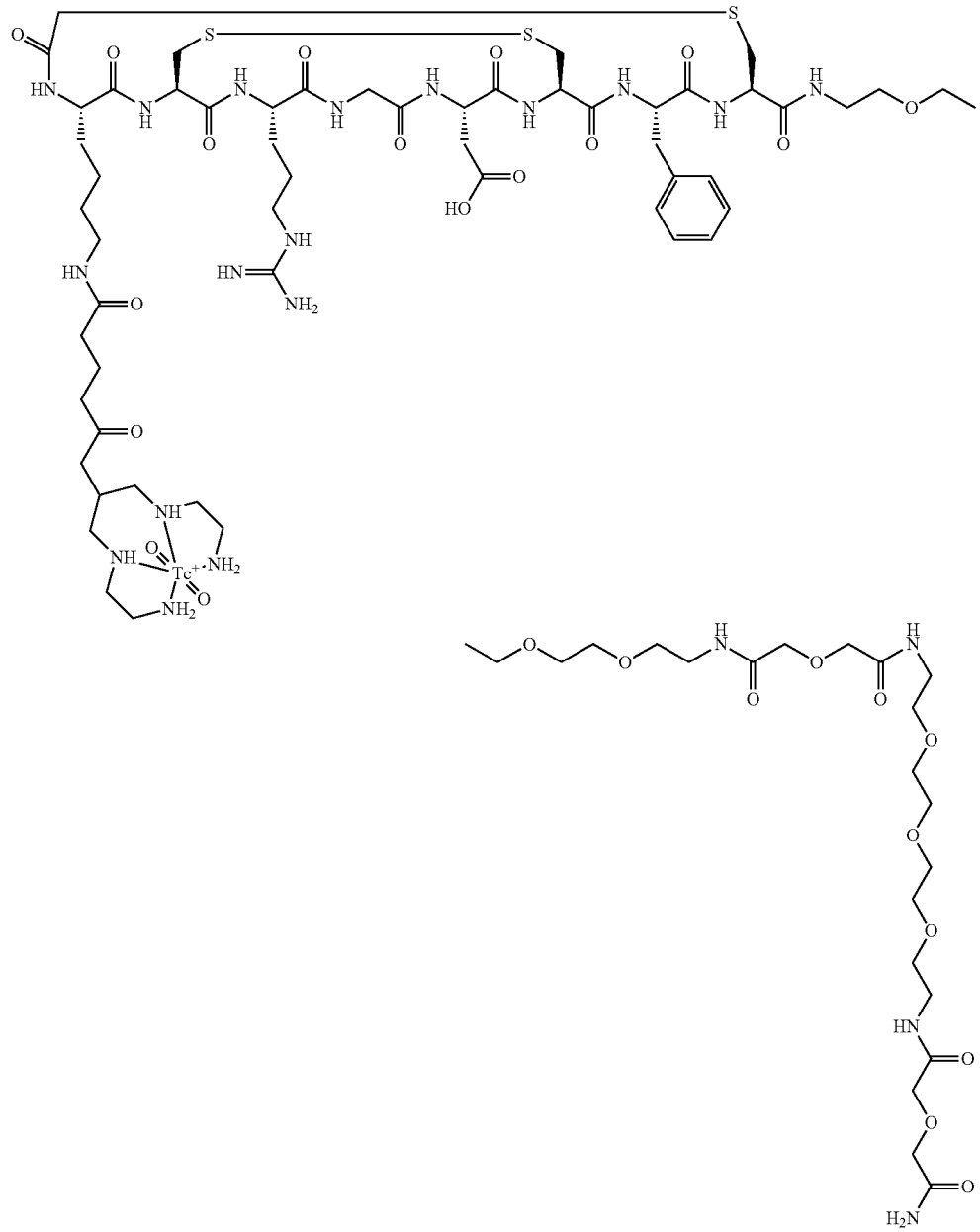

Compound 10a

Methods for the preparation of Compounds 1a-10a are analogous to those for Compounds 1-10, except that the tetraamine chelate of Compounds 1a-10a is used in place of the diamine dioxime chelate of Compounds 1-10. Conjugation of the tetraamine chelate is achieved using normal peptide coupling with a Boc-protected species.

A number of further modified compounds were synthesised with the aim of improving the biodistribution, i.e. primarily to reduce background liver uptake. Details of the synthesis of Compounds 11-15 are provided in Examples 8-12, below. Compound 11 was designed to assess the effect of changing from a diamine dioxime chelate to a tetraamine chelate. In Compound 12 cysteic acid groups were added. Compound 13 has an additional PEG moiety at the N-terminal side of the peptide. Compound 14 has an additional PEG moiety at the C-terminal side of the peptide. In Compound 15 the tetraamine chelate was used in addition to a number of glutamic acid residues.

The method described herein begins by "providing" a subject to whom a detectable quantity of a compound of Formula I has been administered. The purpose of the method of the invention is the provision of a diagnostically-useful image. Therefore, administration to the subject of the compound of Formula I can be understood to be a preliminary step necessary for facilitating generation of said image. Preferably said subject is a mammal, and most preferably a human. Most preferably, said subject is the intact mammalian body in vivo. Therefore, in a preferred embodiment, the compound of Formula I has been administered as a pharmaceutical composition which comprises said compound together with a biocompatible carrier, in a form suitable for mammalian administration. A preferred route of administration is intravascular administration. In an alternative embodiment, administration of a detectable quantity of a compound of Formula I is carried out as part of the method.

Following the providing step and preceding the detection step, the compound of Formula I is allowed to bind to any fibrogenic tissue in said subject. For example, when the subject is an intact mammal, the compound of Formula I will dynamically move through the mammal's body, coming into contact with various tissues therein. Once the compound comes into contact with any fibrogenic tissue, a specific interaction takes place such that clearance of the compound from fibrogenic tissue takes longer than from non-fibrogenic tissue. A certain point in time will be reached when detection of compound specifically bound to fibrogenic tissue is enabled as a result of the ratio between compound bound to fibrogenic tissue versus that bound in non-fibrogenic tissue. An ideal such ratio is at least 2:1.

The "biocompatible carrier" is a fluid, especially a liquid, in which the compound of Formula I is suspended or dissolved, such that the composition is physiologically tolerable, i.e. can be administered to the mammalian body without toxicity or undue discomfort. The biocompatible carrier medium is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). The biocompatible carrier medium may also comprise biocompatible organic solvents such as ethanol. Such organic solvents are useful to solubilise more lipophilic compounds or formulations. Preferably the biocompatible carrier medium is pyrogen-free water for injection, isotonic saline or an aqueous ethanol solution. The pH of the biocompatible carrier medium for intravenous injection is suitably in the range 4.0 to 10.5.

Such pharmaceutical compositions are suitably supplied in either a container which is provided with a seal which is suitable for single or multiple puncturing with a hypodermic needle (e.g. a crimped-on septum seal closure) whilst maintaining sterile integrity. Such containers may contain single or multiple patient doses. Preferred multiple dose containers comprise a single bulk vial (e.g. of 10 to 30 cm$^3$ volume) which contains multiple patient doses, whereby single patient doses can thus be withdrawn into clinical grade syringes at various time intervals during the viable lifetime of the preparation to suit the clinical situation. Pre-filled syringes are designed to contain a single human dose, or "unit dose", and are therefore preferably a disposable or other syringe suitable for clinical use. Where the pharmaceutical composition is a radiopharmaceutical composition, the pre-filled syringe may optionally be provided with a syringe shield to protect the operator from radioactive dose. Suitable such radiopharmaceutical syringe shields are known in the art and preferably comprise either lead or tungsten.

The pharmaceutical composition may be prepared from a kit. Alternatively, it may be prepared under aseptic manufacture conditions to give the desired sterile product. The pharmaceutical composition may also be prepared under non-sterile conditions, followed by terminal sterilisation using e.g. gamma-irradiation, autoclaving, dry heat or chemical treatment (e.g. with ethylene oxide).

In a further aspect of the invention, the compound of Formula I may be employed for use in the preparation of a medicament for the determination of the presence, location and/or amount of fibrogenesis in an organ or body area of a subject. Preferred and most preferred embodiments of Formula I, organ or body area, subject and method of administration are as defined above.

The invention is useful for assessment of the presence, location and/or amount of activated HSC, providing an indicator of fibrogenesis. This is particularly advantageous because fibrogenic tissue is a better marker of early active disease than fibrotic tissue, the latter also being present where the disease process is resolving. Identification of the disease process can therefore be done at a stage when implementation of treatment can be most efficacious.

These advantages are demonstrated in the following non-limiting examples.

BRIEF DESCRIPTION OF THE EXAMPLES

Example 1 demonstrates that Compound 2 binds specifically to activated human HSC in vitro.

Example 2 describes the methods used to set up the rat bile duct ligation model and associated sham-operated model, as well as histopathological validation.

Example 3 demonstrates a correlation between uptake of Compound 4 and fibrogenesis. Markers of fibrogenesis are high in the rat bile duct ligation (BDL) model (described in Example 2) at 15 days postoperatively, and uptake of Compound 4 into fibrogenic livers in rat BDL model is highest at 15 days postoperatively.

Example 4 demonstrates that Compound 4 binding to BDL fibrogenic liver is specifically inhibited by cold Compound 4.

Example 5 demonstrates a correlation between liver uptake of Compound 4 and the liver expression of $\alpha_v$ integrin.

Example 6 shows that Compound 8 binding to BDL fibrogenic liver is specifically inhibited by cold Compound 8.

Example 7 demonstrates a correlation of $\alpha_v$ expression with uptake of Compound 8.

Examples 8-12 describe the synthesis of Compounds 11-15.

Abbreviations Used in the Examples

| | |
|---|---|
| BCA | Bicinchoninic acid assay |
| BDL | Bile duct ligation |
| Boc | tert-Butyloxycarbonyl |
| BSA | Bovine serum albumin |
| DIEA | Diisopropylethylamine |
| DMF | Dimethylformamide |
| EA-Hy966 | Human umbilical vein endothelial cells |
| EGTA | Ethylene glycol tetraacetic acid |
| ESI-MS | Electrospray ionization mass spectrometry |
| FBS | Fetal bovine serum |
| Fmoc | 9H-Fluoren-9-yl methoxycarbonyl |
| MBHA | p-Methylbenzhydrylamine |
| DCC | 1,3-Dicyclohexylcarbodiimide |
| DMSO | Dimethyl sulfoxide |
| HATU | (N-[(Dimethylamino)-1H-1,2,3triazolo-[4,5-b]pyridin-1-ylmethylene]-N-methylmethanaminium hexafluorophosohate N-oxide |
| HPLC | High performance liquid chromatography |
| HOAt | 1-Hydroxy-7-azabenzotriazole |
| HSC | Hepatic stellate cells |
| i.d. | Injected dose |
| i.v. | Intravenously |
| ITLC | Instant thin layer chromatography |
| $K_d$ | Dissociation constant |
| LC-MS | Liquid chromatography-mass spectroscopy |
| NMM | N-Methylmorpholine |
| NMP | 1-methyl-2-pyrrolidinone |

| | |
|---|---|
| NPP | p-Nitrophenyl phosphate |
| PBS | Phosphate-buffered saline |
| PEG | Polyethylene glycol |
| PEI | Polyethylenimine |
| PMSF | Phenylmethylsulphonyl fluoride |
| PyAOP | 7-Azabenzotriazol-1-yloxy)tripyrrolidinophosphonium hexafluorophosphate |
| RIPA | RadioImmuno Precipitation Assay |
| s.c. | Subcutaneously |
| SUV | Standard uptake value |
| TFA | Trifluoroacetic acid |
| UV | Ultraviolet |

EXAMPLES

Example 1

Binding of Compound 6 to Activated Human HSC

1(i) Binding to Membranes Prepared from EA-Hy926 Cells

The inhibition constant of Compound 6 was measured using a previously-described membrane binding assay (Indrevoll et al, Bioorg & Med Chem Lett, 2006, 16, 6190-6193).

In brief, membranes from the human endothelial adenocarcinoma cell line EA-Hy926 were prepared and the $K_d$ calculated for the purified membrane fraction. A competitive binding assay was then established to measure inhibition constants for cold Compound 6. $^{125}$I-echistatin was used as the labelled ligand and cold echistatin as a reference standard.

A total of sixteen dilutions of cold test compound (either cold echistatin or cold Compound 6) were prepared and mixed with a combination of $^{125}$I-echistatin and membrane prior to incubation for 1 hour at 37° C. Following several washes, the bound material was harvested on a filter using a Skatron micro harvester. The filterspots were finally excised and counted in a Packard γ-counter.

FIG. 1 illustrates binding of $^{125}$I-echistatin versus cold Compound 6 and echistatin on EA-Hy926 membranes.

1(ii) Binding to Activated Human Hepatic Stellate Cells

Figure 2:
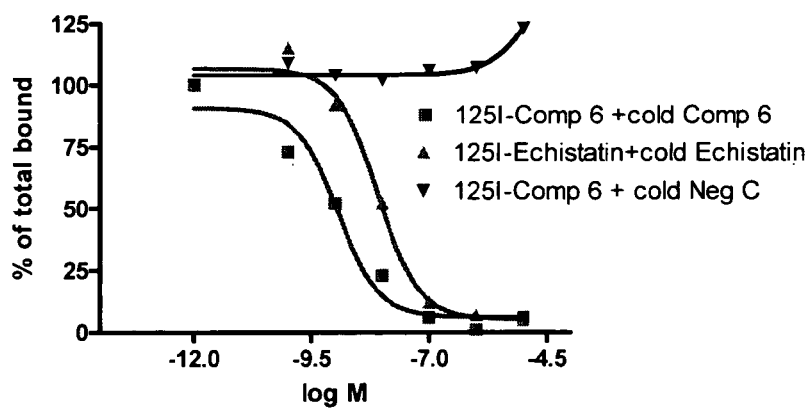

Activated human hepatic stellate cells, LX-2 (provided by Prof. Scott L. Friedman, Mount Sinai School of Medicine, New York), were cultured in 12-well plates (Nunc) to confluence in Dulbeccos Modified Eagels Medium containing 10% FBS, streptomycin and glutamine. The cells were washed twice in a cold buffer containing 50 mM Tris, pH 7.4, 150 mM NaCl, 5 mM MnCl$_2$, 1 mM CaCl$_2$ and 0.01% BSA. The cells were further incubated in the buffer containing a trace amount of labelled compound (either 0.1 nM $^{125}$I Compound 6 or 0.1 nM $^{125}$I-echistatin) together with various concentrations of cold compound for 60 min at 4° C. with shaking. Following incubation, the unbound material was removed by washing the cells 3 times with cold buffer. The cells were detached from the wells by adding 0.1M NaOH and transferred to a tube to be counted in a gamma-counter (Packard). FIG. 2 illustrates the observed activity values.

Example 2

Binding of Compound 3 and Compound 8 to Activated Rat HSC

2(i) Binding to Membranes Prepared from EA-Hy926 Cells

Figure 3:
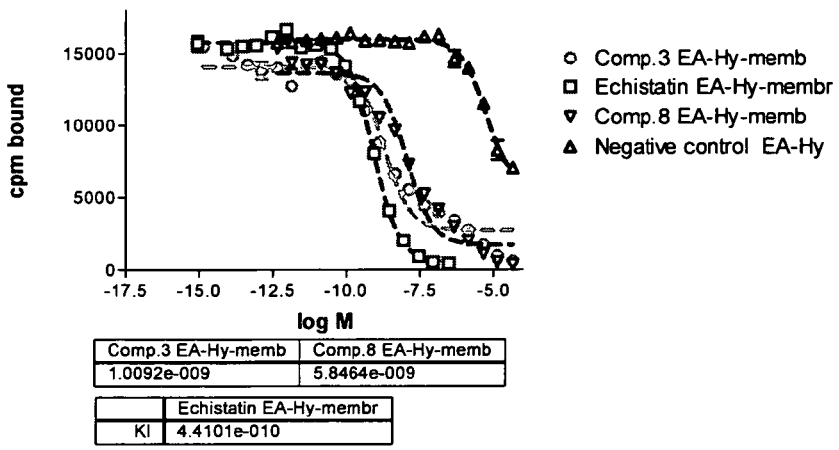
FIG. 3 and FIG. 4 show Compound 3 binding specifically to both activated liver stellate cell membranes and EA-Hy926 membranes. Ki determined as ~1 nM in the EA-Hy926 membrane assay, as observed and 59 nM in the stellate cell membrane assay. Compound 8 seems to follow Compound 3 in affinity, Ki determined to 56 nM in the activated stellate cell membrane assay and 6 nM in the EA-Hy926 membrane assay. The negative control scrambled RGD peptide shows almost no binding to either cell type.

The inhibition constants for Compound 3 and Compound 8 were determined using the method described in Example 1. FIG. 3 illustrates binding of $^{125}$I-echistatin versus cold Compound 3, Compound 8 and echistatin on EA-Hy926 membranes.

2(ii) Cells and Cultivation

An activated rat liver stellate cell line (immortalized) was a kind gift from Professor Trond Berg at University of Oslo. The cells were grown in 150 mm culture flasks to confluence in Dulbeccos modified Eagels medium containing 10% FBS, glutamine and Penicillin/Streptomycin.

2(iii) Preparation of Membranes

The cells were washed twice in ice cold PBS, pH 7.4, added 10 ml PBS and scraped off with a rubber policeman and transferred to a 50 ml vial on ice. Another 10 ml PBS were added to the flasks, scraped and combined with the first cells. The cells were centrifuged at 2000 rpm at 4° C. for 10 min. The supernatant was poured off and the pellet resuspended in 3 ml PBS. All pellets were combined into one tube, centrifuged as above and the final pellet frozen at −70° C. immediately.

The cell pellets were resuspended in ice-cold homogenization buffer (10 times the amount of cells, for example 2 g pellet to 20 ml homogenization buffer) containing 50 mM Tris-HCl, 5 mM MgCl$_2$, 1 mM EGTA, pH7.4 and in addition protease inhibitors 10 ug/ml leupeptin, 10 ug/ml pepstatin, 200 ug/ml Bacitracin, 0.5 ug/ml aprotinin and 100 uM PMSF. The cells were homogenized on ice with 3 times 10 strokes in a Dounce homogenizer, pestle B. The homogenate was centrifuged for 5 min at 2100 rpm at 4° C. and the supernatant was poured off. The pellet was resuspended in 10 ml homogenization buffer and rehomogenized 2 times 10 strokes before centrifugation at 2100 rpm in 10 min. This supernatant was combined with the first one and centrifuged at 16500 rpm in a Beckman Coulter Centrifuge with JA-17 rotor (29000×g). The pellet was resuspended in 20 ml homogenization-buffer and the centrifugation step was repeated.

The supernatant was poured off and the pellet resuspended in 3 ml binding buffer containing 10 mM Hepes, 135 mM NaCl, 4.8 mM KCl, 1.7 mM MgSO$_4$, 2.5 mM CaCl$_2$, 1.0 mM NaH$_2$PO$_4$, pH 7.4. Following removal of samples for protein measurements, 3 ml more of binding buffer was added. Aliquots of 300 ul were frozen immediately at −80° C.

2(iv) Protein Measurement 100 ul of the well mixed membrane prep was diluted 1:10 and a serial dilution and the protein content measured according to the instructions in BCA Protein Assay Reagent kit (Pierce No. 23225).

Figure 4:
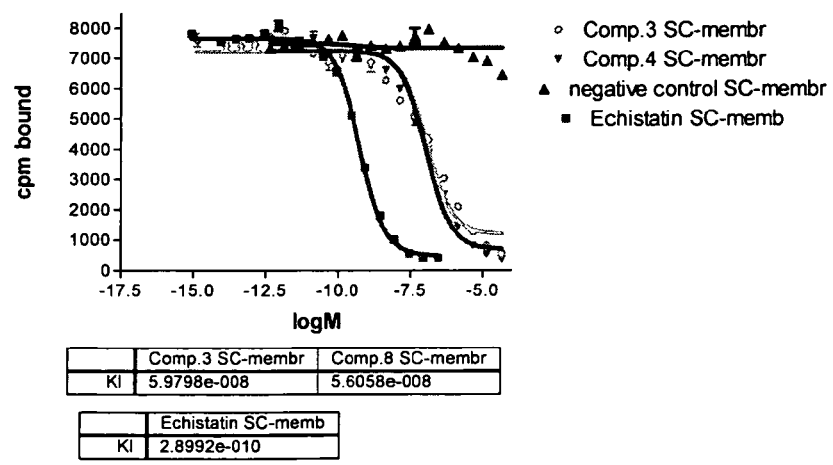

2(v) Experimental Design Testing Binding to Integrins on Stellate Cell Membranes An experiment was set up in a 96-well plate. To each well 60 ul buffer (50 mM Tris, pH 7.4, 150 mM NaCl, 5 mM MnCl$_2$, 1 mM CaCl$_2$, 0.01% BSA), 20 ul cold Compound 3, Compound 8 or cold echistatin, 20 ul $^{125}$I-echistatin and 50 ul membrane solution (diluted 1:30 in buffer corresponding to about 1ug membrane per well) were added and incubated at 37° C. for 60 min with shaking. Following incubation, unbound material was washed away with PBS in a Skatron cell harvester and the bound material concentrated into a filter spot. This filterspot was cut off and added a tube that finally was counted in a gamma-counter. The filters were pre-soaked in 0.3% PEI in water for at least 4 hours. FIG. 4 shows the results obtained.

Example 3

Bile Duct Ligation (BDL) and Sham Animals

3(i) Animal Model Set-Up

Outbred male Sprague Dawley rats (180-200 g; Charles River) were used in all bile duct ligation (BDL) and sham studies. After 6 days acclimatization rats were divided into 2 groups (BDL group and sham group).

For the BDL animals, the abdomen was shaved and swabbed with betadine solution followed by 5 mg/kg carprofen subcutaneously (s.c.) and 5 mg/kg bupronorphine s.c. and under Isoflurane anaesthesia a mid-line laparotomy was performed and the common bile duct located. Bile duct was double ligated, the first ligation made between the junction of the hepatic ducts and the second above the entrance of the pancreatic ducts.

The second group (sham animals) abdomen was shaved and swabbed with betadine solution followed by 5 mg/kg carprofen s.c. and 5 mg/kg bupronorphine s.c. Animals underwent sham surgery where bile duct was manipulated and a suture passed under the bile duct.

Before closing 2-3 ml saline was administered into the peritoneum of each animal. Fascia and skin were closed and animals administered with 2 mg/kg metaclopromide s.c, 5 mg/kg Baytril s.c., and ~2 ml saline s.c. Carprofen was given (5 mg/kg) as required over the next couple of days. Animals were closely monitored for the duration of the experiment.

3(ii) Administration of Test Compound and Biodistribution

On the appropriate day post surgery BDL and sham animals were removed and put under isoflurane anaesthesia, then each animal was injected with 0.3 ml intravenously (i.v.) via tail vein (~3MBq). At the appropriate time point post-injection of the test item, each animal was re-anaesthetised with isoflurane, sacrificed by cervical dislocation weighed and the weight recorded via a barcode scanning system. Each animal was dissected and the following organs and tissues were removed and counted using BASIL counter protocol 40 or manual counting:

| | |
|---|---|
| Bone* | Muscle* |
| Blood* | Kidneys |
| Bladder & Urine (B/U) | Lung |
| Liver* | Spleen |
| Stomach & contents | Small and large intestine (SI & LI) |
| Heart | Thyroid |
| Skin* | Carcass |
| Injection site | |

*weighed samples

The recorded activity in a whole organ (e.g., liver) was corrected for background radioactivity and for radioactive decay and the biodistribution of radioactivity calculated by reference to Formula I:

$$\% \text{ i.d. Organ} = \frac{A}{B} \times 100$$

where:
A=counts per second measured in organ
B=total counts per second measured in all samples (excluding the injection site)

The percentage of injected radioactivity in the weighed tissue samples (e.g., blood) was calculated to give % i.d. in the entire tissue by reference to Formula 2:

$$\% \text{ i.d. tissue} = \frac{(Z_s \times W_b \times F)/B}{W_s} \times 100$$

where:
$Z_s$=counts per second in sample
$W_s$=weight of sample in grams
$W_b$=weight of animal in grams immediately after sacrifice
B=total counts per second measured in all the samples (excluding the injection site)
F=tissue specific factor representing the mass of the tissue as a proportion of the total body weight of the animal

| Tissue | F |
|---|---|
| Bone | 0.05 |
| Muscle | 0.43 |
| Blood | 0.058 |
| Skin | 0.18 |
| Fat | 0.07 |

3(iii) Histopathological Evaluation

Sections from the liver of each animal were fixed in 10% buffered neutral formalin solution at room temperature, embedded in paraffin, and 5-μm thick sections were prepared. Sections were stained with Mayer's Hematoxylin and Eosin (H&E) for evaluation of biliary hyperplasia, necrosis and inflammation, and Gomori's trichrome stain for fibrosis (collagen stain) using standard staining protocols previously described (Gomori 1950 Am. J. Clin. Pathol, 20:661-663).

Histological grading of liver damage was assessed by semi-quantitatively by evaluating the extent and severity of each lesions, then scoring the lesion from 0-5 as follows: no lesion=0, minimal=1, mild=2, moderate=3, marked=4, severe=5. Histomorphological evaluation of the tissues was performed on a blind basis with respect to both days post surgery, and procedure (i.e. sham vs. bile duct ligation). All data were peer reviewed by an additional pathologist. Histological analysis was performed by light microscopy. Sections were viewed under bright-field illumination using a 40×, 100× or 400× objective lens.

Table 4 Summarises the Histopathological Evaluation:

TABLE 4

| Treatment | Pathology | Day 3 | Day 5 | Day 10 | Day 15 | Day 28 |
|---|---|---|---|---|---|---|
| Sham | All | 0 | 0 | 0 | 0 | 0 |
| BDL | Biliary Hyperplasia | 1 | 1 | 2 | 3 | 3 |
| | Inflammation | 0/1 | 0/1 | 0/1 | 0/1 | 0/1 |
| | Necrosis | 1 | 0/1 | 0/1 | 0/1 | 0/1 |
| | Fibrosis | 1 | 2 | 4 | 4 | 2 |

The data presented supports the use of this model, particularly at day 15, as a suitable model of hepatic fibrosis in which to identify molecules which show specific uptake associated with fibrogenesis.

Example 4

Compound 8 Taken Up into Fibrogenic Livers in Rat BDL Model (@15 Days When Markers of Fibrogenesis are High) Vs. Sham The BDL and sham animal models were set up as described in Example 3. Uptake of Compound 8 was calculated as Standard Uptake Value (SUV) as follows:

$$SUV = \frac{(Z_s/W_s)}{(Z_t/W_t)}$$

$Z_s$=counts per second in sample
$W_s$=weight of sample in grams
$Z_t$=total counts per second measured in all the samples (excluding the injection site)
$W_t$=weight of animal in grams The percentage of radioactivity in the carcass was calculated by reference to the counts/second in the residual carcass after dissection and correcting for the sampled tissues remaining in the carcass. Biological variability in body composition may have resulted in slight inaccuracies in the estimation of the tissue values and hence possible over- or under-correction of the carcass value. Where the carcass value has been over-corrected this occasionally resulted in negative values.

Figure 5:
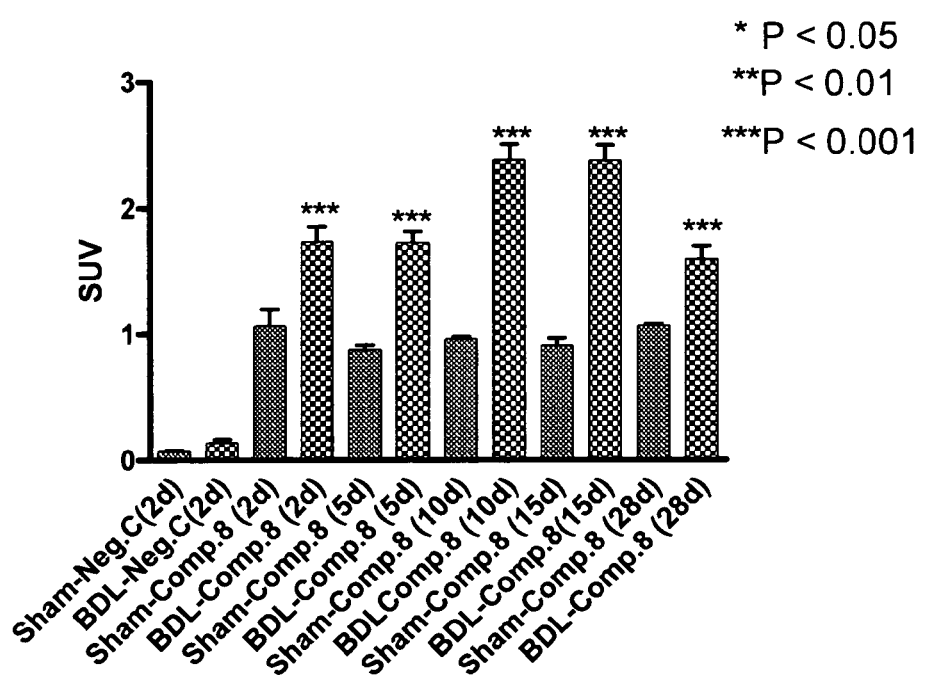
FIG. 5 demonstrates specific uptake of Compound 8 by livers from bile duct ligation (BDL) rats compared to negative control scrambled RGD peptide, where no liver uptake was observed. The BDL liver uptake was also proportional to the degree of fibrogenesis, with maximum uptake being observed at 10 and 15 days post-surgery when fibrogenesis is at its highest level.

FIG. 5 summarises the retention of radioactivity expressed as SUV in the livers of BDL- and sham-operated animals 1 hour of tail vein injection of Compound 8 at one of 2, 5, 10, 15, 28 days post-operatively, and a scrambled negative control (structure below) at 2 days post-operatively.

Example 5

At 15 Days Post-Op in BDL Model, Compound 3 and Compound 8 are Taken Up into Fibrogenic Livers Vs. Sham Animals and Vs. Negative Control The BDL and sham animal models were set up as described in Example 3. At 15 days post-operatively, one of Compound 3, Compound 8 or a negative control was administered to each animal and liver uptake assessed as described in Example 3.

The structure of the negative control was as follows:

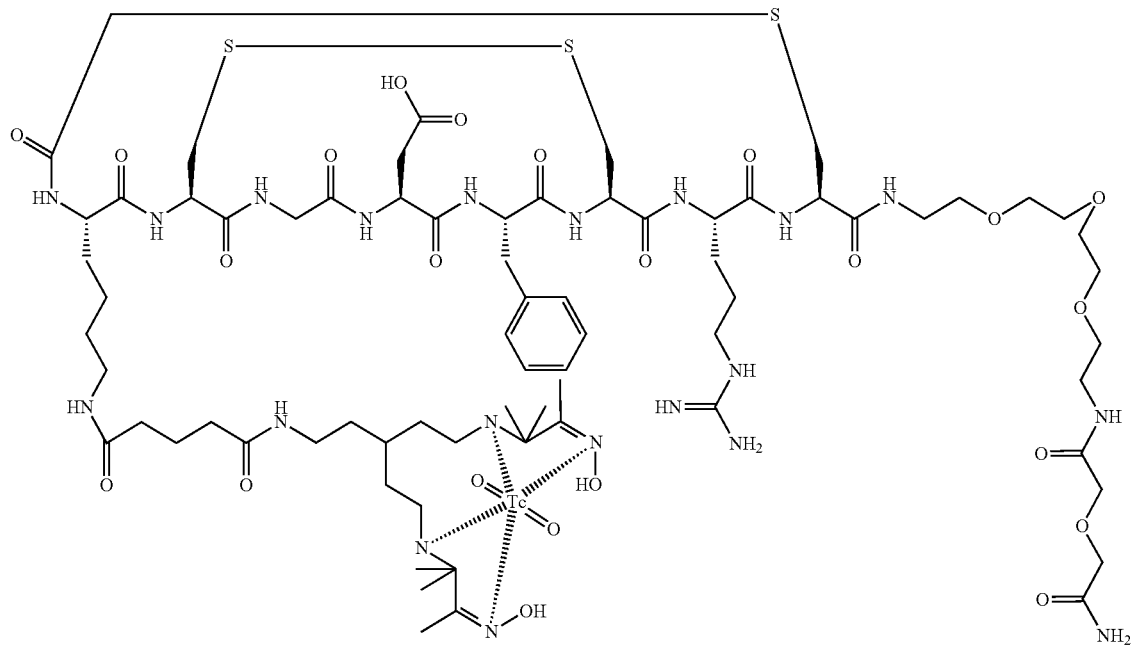

The results demonstrate significant retention of radioactivity in BDL as compared with sham-operated animals at all time points tested with the maximum retention of radioactivity observed in the livers from BDL animals at 10 and 15 days post-operatively. There was no significant difference in liver uptake in the sham-operated animals at any time point post-operatively.

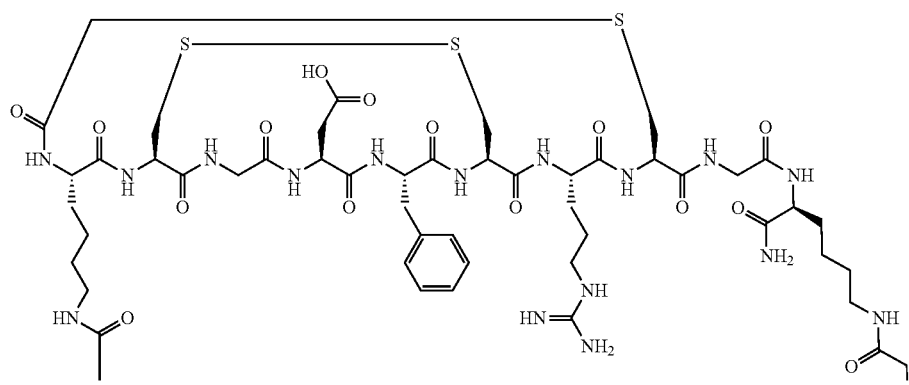

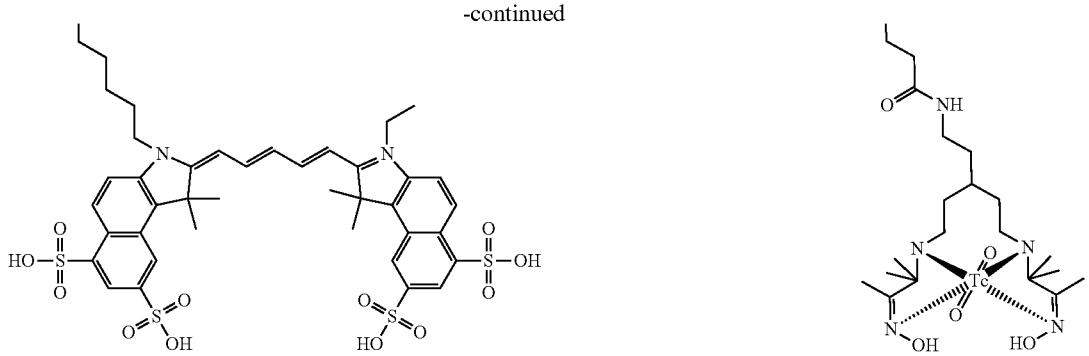

Figure 6:
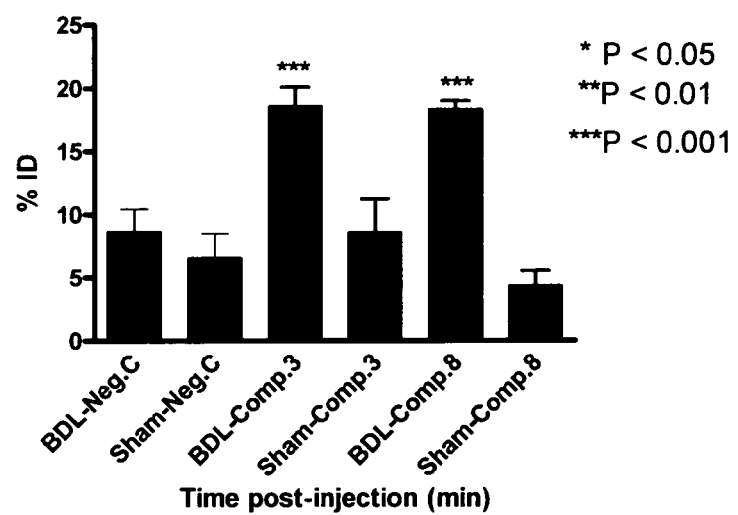
FIG. 6 illustrates specific uptake of RGD-peptide into BDL rat liver vs. a negative control compound (RGD scrambled peptide). Data from this experiment showed that both Compound 3 and Compound 8 were significantly retained in the liver of BDL compared to sham animals at one hour post-injection compared to the negative control where no significant difference in uptake between BDL and sham was observed.

FIG. 6 illustrates significantly higher liver uptake of Compounds 3 and 8 in the BDL model as compared with the sham-operated animals.

Example 6

Compound 8 Binding to BDL Fibrogenic Liver is Specifically Inhibited by Cold Compound 8

The biodistribution of radioactivity was investigated in 15 days post-operatively in BDL and sham-operated male Sprague Dawley rats (procedures described in Example 3) 1 hour following of intravenous injection via tail vein of ~3 MBq of Compound 8, both before and after addition of 1:100 and 1:10,000 fold excess of cold Compound 8. At the appropriate time point post-injection of the test Item, each animal was re-anaesthetised with isoflurane, sacrificed by cervical dislocation and weighed. Each animal was dissected and organs and tissues (see Tables 5 and 6 below) were removed and counted using BASIL counter protocol 40 or manual counting.

The principal sites of accumulation of activity (in % i.d.) at one hour post-injection the BDL animals are summarized in Table 5 below:

TABLE 5

| BDL 60 minutes | Compound 8 | | 100-fold excess | | 10K-fold excess | |
|---|---|---|---|---|---|---|
| | Mean | SD± | Mean | SD± | Mean | SD± |
| Bone | 3.02 | 0.53 | 2.97 | 0.16 | 3.18 | 0.40 |
| Muscle | 10.76 | 2.37 | 8.76 | 0.19 | 9.61 | 1.40 |
| Blood | 1.47 | 0.15 | 1.61 | 0.09 | 1.60 | 0.13 |
| Kidneys | 3.78 | 0.08 | 4.20 | 0.26 | 3.61 | 0.29 |
| Bile & Urine | 40.98 | 0.37 | 38.27 | 0.70 | 41.58 | 6.57 |
| Lung | 0.43 | 0.02 | 0.50 | 0.01 | 0.50 | 0.08 |
| Liver | 12.73 | 7.10 | 16.10 | 3.33 | 9.81 | 2.08 |
| Spleen | 0.51 | 0.00 | 0.57 | 0.04 | 0.52 | 0.10 |
| Stomach | 0.89 | 0.07 | 0.96 | 0.12 | 1.69 | 0.72 |
| Small & Large Intestine | 8.32 | 1.50 | 7.41 | 0.48 | 8.58 | 1.73 |
| Heart | 0.13 | 0.00 | 0.13 | 0.01 | 0.14 | 0.01 |
| Thyroid | 0.04 | 0.02 | 0.04 | 0.02 | 0.06 | 0.01 |
| Skin | 12.58 | 2.02 | 12.02 | 0.41 | 12.99 | 0.63 |
| Carcass | 4.36 | 0.88 | 6.47 | 1.83 | 6.14 | 0.60 |
| Injection Site | 1.32 | 0.26 | 1.75 | 0.35 | 1.68 | 0.07 |

The principal sites of accumulation of activity (in % i.d.) at one hour post-injection the sham animals are summarized in Table 6 below:

TABLE 6

| BDL 60 minutes | Compound 8 | | +100-fold excess | | +10K-fold excess | |
|---|---|---|---|---|---|---|
| | Mean | SD± | Mean | SD± | Mean | SD± |
| Bone | 3.10 | 0.19 | 3.06 | 0.63 | 2.42 | 0.10 |
| Muscle | 10.43 | 0.82 | 10.92 | 0.40 | 8.41 | 1.02 |
| Blood | 1.55 | 0.14 | 1.37 | 0.09 | 1.40 | 0.16 |
| Kidneys | 4.07 | 0.13 | 4.13 | 0.11 | 3.65 | 0.52 |
| Bile & Urine | 44.65 | 2.79 | 43.25 | 2.87 | 46.52 | 4.68 |
| Lung | 0.46 | 0.07 | 0.38 | 0.04 | 0.39 | 0.05 |
| Liver | 3.71 | 0.66 | 3.52 | 0.39 | 3.03 | 0.31 |
| Spleen | 0.29 | 0.02 | 0.29 | 0.06 | 0.27 | 0.02 |
| Stomach | 0.90 | 0.11 | 1.21 | 0.15 | 1.92 | 1.07 |
| Small & Large Intestine | 7.86 | 0.12 | 8.42 | 0.60 | 7.54 | 1.01 |
| Heart | 0.12 | 0.02 | 0.10 | 0.01 | 0.10 | 0.01 |
| Thyroid | 0.05 | 0.02 | 0.05 | 0.00 | 0.04 | 0.01 |
| Skin | 14.37 | 0.71 | 13.97 | 0.93 | 12.69 | 1.37 |
| Carcass | 8.45 | 0.67 | 9.32 | 1.01 | 11.63 | 1.90 |
| Injection Site | 1.66 | 0.12 | 1.44 | 0.06 | 1.71 | 0.15 |

Example 7

Compound 8 Uptake and Alpha-v Upregulation in BDL Day 15

The BDL and sham animal models were set up as described in Example 3. At each of 2, 15 and 28 days post-operatively, ~3 MBq Compound 8 was administered to animals and the liver uptake assessed as described in Example 3.

The expression of $\alpha_v$ integrin in the animals' livers was measured in homogenised livers of BDL- and sham-operated animals. At each of 2, 15 and 28 days post-operatively, animals were sacrificed and their livers removed and stored at −70° C.

Pre-weighed livers were removed from −70° C. freezer and placed into pre-cooled mortar and pestle in the presence of low amount of liquid nitrogen. Liver was crushed to almost a homogenous powder (during the crushing of the liver a small amount of liquid nitrogen was added to keep the tissue frozen at all times). The crushed livers were placed into a pre-cooled medicine measure and put into −70° C. freezer until further use. 1 g of frozen crushed tissue was added directly into 10 ml of ice cold RIPA buffer (Sigma; 150 mM NaCl, 1.0% Igepal CA-630 (detergent), 0.5% sodium deoxycholate (anionic detergent), 0.1% SDS, 50 mM Tris, pH 8.0) containing 1 mM EDTA, 0.25M sucrose and freshly added protease inhibitor cocktail (Sigma) (10 μl cocktail/ml of lysis buffer). The mixture was homogenized with a sharp blade homogenizer at 4° C. and kept on wet ice for 30 minutes.

The homogenate was transferred into a pre-chilled glass tissue Dounce and three up and down strokes of the pestle were applied at 4° C. The tissue homogenate was then transferred into pre-cooled centrifuge tubes and centrifuged for 30 minutes at 30,000 rpm and 4° C. Supernatants were removed (total cell lysate) and placed on wet ice. Relative protein concentration was determined in each sample using a commercial protein assay kit with BSA standards according to the manufacturer's instruction (Pierce, USA) (BSA aliquots should be made in modified RIPA buffer that was used for the homogenisation). Supernatant from each sample was further diluted between 1:50 and 1:200 in $H_2O$ and protein concentration was determined using a 99 multi-well Plate reader (iEMS). Each sample was divided into 1 ml aliquots and stored at −70° C. until further use.

Anti-alpha-v integrin capture antibody (BD; catalogue number: 611013) was diluted to appropriate concentration in binding solution (0.05 M tris, 0.138 M NaCl and 0.0027 M KCl) and either 50 or 100 µl was added to each well of an enhanced protein-binding ELISA plate (Nunc-Immuno™ plates 96-well plate, MaxiSorp). The amount of antibody used was 200 ng/well. Plates were sealed and incubated either for 1 hour at 37° C. or overnight at 4° C. Plates were emptied and the remaining sites for protein binding on the microtiter plate were saturated by incubating with blocking buffer (3% BSA/TBS with 0.02% sodium azide approx. 300 µl per well). Plates were sealed and incubated for 1 hour at 37° C. then washed 3 times with TBS/0.01% Tween-20. Neat liver homogenate supernatant and/or different concentrations of purified alpha-v integrin standards were prepared in blocking buffer and added in triplicate (100 µl per well) into the coated plates then sealed and incubated for 2 hrs at 37° C. Plates were washed 4 times with TBS/0.05% Tween-20 and a second anti-integrin detection antibody (Chemicon AB1930) diluted in blocking buffer was added to wells and incubated for 1 hour at 37° C. Plates were washed 4 times with TBS/0.05% Tween-20 and secondary antibody alkaline phosphatase conjugated (Sigma; catalogue number: A7539) specific to the detection antibody was added to the wells and incubated for 1 hr at 37° C. Plates were washed 4 times with TBS/0.05% Tween-20 and 100 µl of NPP substrate solution to each well and incubate either for 2 hr at room temperature or overnight at 4° C. Hydrolysis was monitored qualitatively by visual inspection or quantitatively with a microtiter plate reader. Hydrolysis of NPP appears yellow after suggested incubation time has elapsed, optical densities at target wavelengths (405 nm) was measured on an ELISA plate reader (Spectra-Max Plus). Hydrolysis was stopped by adding 50 µl of 5 M sodium hydroxide NaOH.

For quantitative results, the signal of unknown samples was compared against those of the standard curve. Statistical analyses were performed using GraphPad PRISM, Version 4.0. Differences between groups were analysed by the non-parametric One-Way ANOVA. In all statistical analyses, a probability value of less than 0.05 ($P<0.05$) was considered significant.

Figure 7:
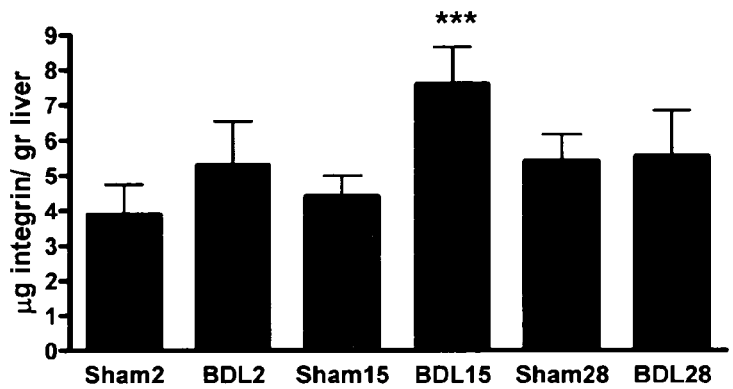
FIG. 7 shows significant alpha$_v$-integrin up-regulation in BDL on day 15 post-op. In conjunction with FIG. 7, FIG. 8 demonstrates correlation between alpha$_v$-integrin expression and compound uptake in liver of BDL animals at all time point post-surgery.
Figure 8:
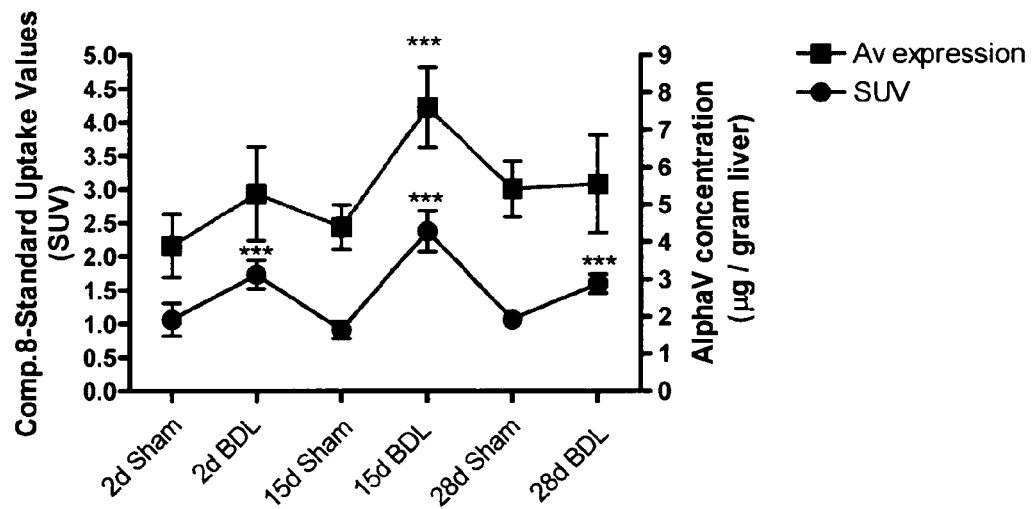

FIG. 7 and FIG. 8 illustrate $\alpha_v$ expression in BDL vs. sham animals and demonstrate a correlation of $\alpha_v$ expression with uptake of Compound 8.

Example 8

Synthesis of Compound 11

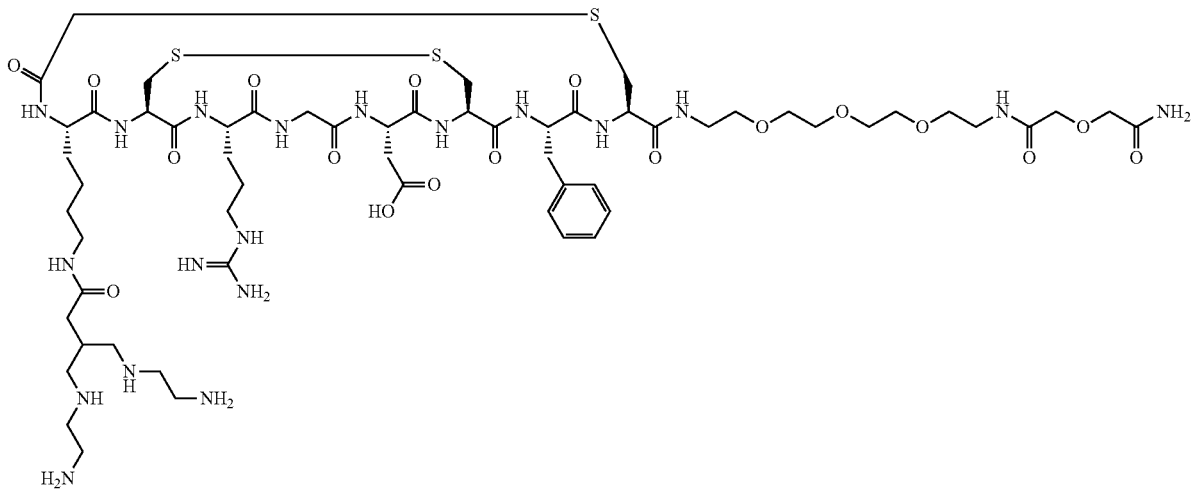 [SMILES: N=C(N)NCCC[C@@H]1NC(=O)[C@@H]2CSSC[C@H](NC(=O)[C@H](CC(=O)O)NC(=O)CNC1=O)C(=O)N[C@@H](Cc1ccccc1)C(=O)N[C@H](C(=O)NCCOCCOCCOCCNC(=O)COCC(N)=O)CSCC(=O)N[C@@H](CCCCNC(=O)CC(CNCCN)CNCCN)C(=O)N2]

Boc-tetraamine-N-hydroxysuccinimide ester (WO 2006/008496) (36 mg, 0.050 mmol) was preactivated with HOAt (1.4 mg, 0.010 mmol) and NMM (17 µL, 0.15 mmol) in DMF (0.5 mL) for 10 min and then added to a solution of Cyst-6; c[$CH_2$CO-Lys-Cys-Arg-Gly-Asp-Cys-Phe-Cys]-PEG(4)-Diglycoloyl-$NH_2$ (WO 03/006491) (12.6 mg, 0.010 mmol) in DMF (0.5 mL). The reaction mixture was stirred at room temperature for 3 days then concentrated in vacuo. The Boc protection groups were removed by addition of a TFA/water/triisopropylsilane (95:2.5:2.5, 10 mL) solution for 90 min. The mixture was concentrated and the crude product was precipitated from ether and purified by preparative HPLC (column Phenomenex Luna C18(2) 250×21.2 mm, 5 µm, solvents: A=water/0.1% TFA and B=acetonitrile/0.1% TFA; gradient 10-20% B over 40 min; flow rate 10 mL/min, UV detection at 214 nm and 254 nm) affording 10.4 mg after lyophilisation. Analysis by LC-MS (column Phenomenex Luna C18(2) 20×2 mm, 3 µm, solvents: A=water/0.1% TFA and B=acetonitrile/0.1% TFA; gradient 10-20% B over 5 min; flow rate 0.6 mL/min, UV detection at 214 and 254 nm, ESI-MS) $t_R$=2.02 min, m/z 1458.7 $(MH)^+$ confirmed the structure.

Labelling with $^{99m}Tc$ was carried out by adding the following to a nitrogen-purged P46 vial: 100 µg of IGF precursor 1 or 2 in MeOH: 0.5 ml Na, CO/$NaHCO_3$ buffer (pH 9.2); 0.5 ml $TcO_4^-$ from a Drytec™ $^{99m}Tc$ generator; 0.1 ml $SnCl_2$/

MDP solution (containing 10.2 mg SnCl$_2$ and 101 mg methylenediphosphonic acid in 100 ml N$_2$ purged saline).

Example 9

Synthesis of Compound 12

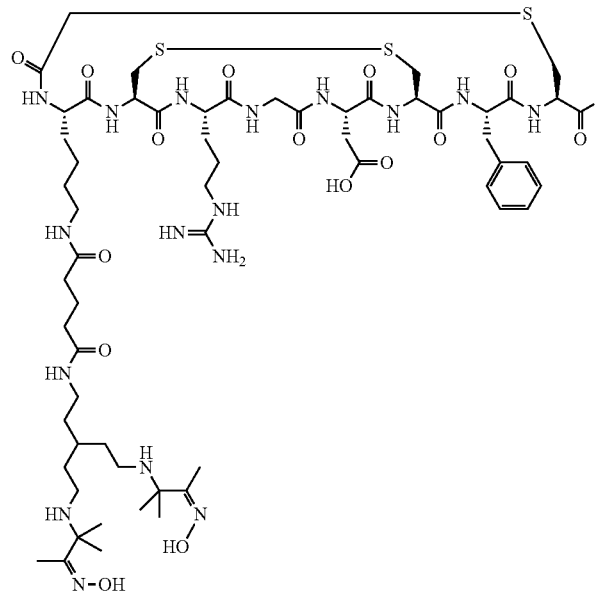

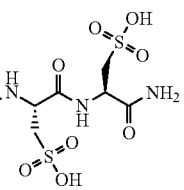

The synthesis was run on a Rink amide AM resin on 0.3 mmol scale (0.432 g, loading 0.71 mmol/g). The first three coupling steps were carried out in a manual nitrogen bubbler apparatus. The Fmoc group on the resin was cleaved by standard protocol (20% piperidine in DMF). Fmoc-Cys (trityl)-OH (702 mg, 1.20 mmol) was coupled to the resin in DMF by standard coupling reagents HATU and DIEA. Completion of coupling was checked by standard Kaiser test. After Fmoc cleavage the coupling was repeated introducing the second cysteine. The resin was suspended in a dichloromethane/TFA/triisopropylsilane (94:5:1, 10 mL) solution. After 3 min the yellow solution was drained off. The step was repeated 6 times assuring complete deprotection of the side chain thiol functions. The resin was washed with dichloromethane and dried (nitrogen flow for 30 min). A mixture of 20% formic acid (18 mL) and 35% hydrogen peroxide (2 mL) was allowed to stand for 1 h at room temperature and then cooled to 0° C. The resin was washed with an aliquot of the performic acid solution (2×4 mL) and then kept in the performic acid solution (5 mL) for 12 h at 5° C. with gentle shaking. An aliquot of the resin was cleaved (TFA/water/triisopropylsilane, 95:2.5:2.5) and analysed by LC-MS (column Phenomenex Luna C18(2) 50×2 mm, 3 μm, solvents: A=water/0.1% TFA and B=acetonitrile/0.1% TFA; gradient 5-50% B over 5 min; flow rate 0.3 mL/min, UV detection at 214 and 254 nm, ESI-MS) $t_R$=2.48 min, m/z 564.3 (MNa)$^+$ confirming the structure.

After Fmoc removal (standard protocol) of the resin above, Fmoc-amino-PEG(4)-Diglycolic acid (796 mg, 1.50 mmol) was coupled to the resin in DMF using standard coupling reagents (HATU and DIEA). After 6 h an aliquot was cleaved (described in previous paragraph) and analysed by LC-MS (column Phenomenex Luna C18(2) 50×2 mm, 3 μm, solvents: A=water/0.1% TFA and B=acetonitrile/0.1% TFA; gradient 5-50% B over 5 min; flow rate 0.3 mL/min, UV detection at 214 and 254 nm, ESI-MS) $t_R$=3.28 min, m/z 832.3 (MH)$^+$ showing complete conversion.

All subsequent amino acids were coupled using an ABI433A automated peptide synthesiser using SlowMoc coupling protocol on ~0.25 mmol resin from above to give H-Lys(Boc)-Cys(tBu)-Arg(Pmc)-Gly-Asp(OtBu)-Cys(tBu)-Phe-Cys(Trt)-PEG4-Diglycoloyl-CyA-CyA-Rink amide resin.

A solution of chloroacetic acid (142 mg, 1.50 mmol) and DCC (155 mg, 0.75 mmol) in dichloromethane (10 mL) was stirred at room temperature for 15 min, then filtered and concentrated. The residue was taken up in DMF and added to the peptide resin above. The peptide was cleaved off the resin using a TFA/water/triisopropylsilane solution (95:2.5:2.5, 10 mL) for 2 h. The solution was concentrated and the crude peptide precipitated from ether and dried in vacuo to give 340 mg. Analysis by LC-MS (column Phenomenex Luna C18(2) 50×2 mm, 3 μm, solvents: A=water/0.1% TFA and B=acetonitrile/0.1% TFA; gradient 0-50% B over 5 min; flow rate 0.3 mL/min, UV detection at 214 and 254 nm, ESI-MS) $t_R$=3.09 min, m/z 1710.6 (MH)$^+$ confirmed the chloroacetylated peptide.

To a solution of the peptide (68 mg) in 50% acetonitrile (64 mL) was added 2.5% ammonia until pH was 8.5. The mixture was stirred at room temperature for 16 h. LC-MS analysis confirmed complete thioether cyclisation. Acetonitrile was removed under reduced pressure and the aqueous solution was lyophilised. Isolated material was taken up in a 5% solution of DMSO in TFA (100 mL) and stirred at room temperature for 60 min. The mixture was concentrated and the crude product isolated by precipitation from ether followed by purification by preparative HPLC (column Phenomenex Luna C18(2) 250×21.2 mm, 5 μm, solvents: A=water/0.1% TFA and B=acetonitrile/0.1% TFA; gradient 5-20% B over 60 min; flow rate 10 mL/min, UV detection at 214 and 254 mil) to give 48 mg of solid material. Analysis by LC-MS (column Phenomenex Luna C18(2) 50×2 mm, 3 μm, solvents: A=water/ 0.1% TFA and B=acetonitrile/0.1% TFA; gradient 0-30% B over 5 min; flow rate 0.3 mL/min, UV detection at 214 and 254 nm, ESI-MS) $t_R$=3.18 min, m/z 1560.5 (MH)$^+$ confirmed the disulfide bridge formation.

A partially dissolved mixture of the peptide (5 mg), Chelate I-Glutaryl tetrafluorothiophenol ester (WO 03/006491) (5 mg) and DIEA (2.7 μL) in NMP (1.5 mL) was heated at 40° C. overnight. The mixture was purified by preparative HPLC (column Phenomenex Luna C18(2) 250×21.2 mm, 5 μm, solvents: A=water/0.1% TFA and B=acetonitrile/0.1% TFA; gradient 0-30% B over 40 min; flow rate 10 mL/min, UV detection at 214 and 254 nm) affording 2.9 mg pure product. Analysis by LC-MS (column Phenomenex Luna C18(2) 20×2 mm, 3 μm, solvents: A=water/0.1 TFA and B=acetonitrile/0.1% TFA; gradient 0-30% B over 5 min; flow rate 0.6 mL/min, UV detection at 214 and 254 nm, ESI-MS) $t_R$=3.83 min, m/z 1000.7 (MH$_2$)$^{2+}$ confirmed the structure.

Labelling with $^{99m}$Tc was carried out as described in WO 2003/006491.

Example 10

Synthesis of Compound 13 parative HPLC (column Phenomenex Luna C18(2) 250×21.2 mm, 5 μm, solvents: A=water/0.1% TFA and B=acetonitrile/0.1% TFA; gradient 10-30% B over 40 min; flow rate 10 mL/min, UV detection at 214 and 254 nm) affording 5.5 mg. Analysis by LC-MS (column Phenomenex Luna C18(2) 20×2 mm, 3 μm, solvents: A=water/0.1% TFA and B=acetonitrile/0.1% TFA; gradient 10-25% B over 5 min; flow rate 0.6 mL/min, UV detection at 214 and 254 um, ESI-MS) $t_R$=3.01 min, m/z 1636.0 (MH)$^+$ confirmed the product.

Chelate 1-Glutaric acid (WO 03/006491) (15.6 mg, 0.034 mmol) was coupled to the peptide (5.5 mg, 0.0034 mmol) in DMF using standard coupling reagents (PyAOP (7-Azabenzotriazol-1-yloxy-tris-(pyrrolidino)phosphonium hexafluorophosphate) and NMM). After 4 h the mixture was purified by preparative HPLC (column Phenomenex Luna C18(2) 250×21.2 mm, 5 μm, solvents: A=water/0.1% TFA and B=acetonitrile/0.1% TFA; gradient 15-30% B over 40 min; flow rate 10 mL/min, UV detection at 214 and 254 nm)

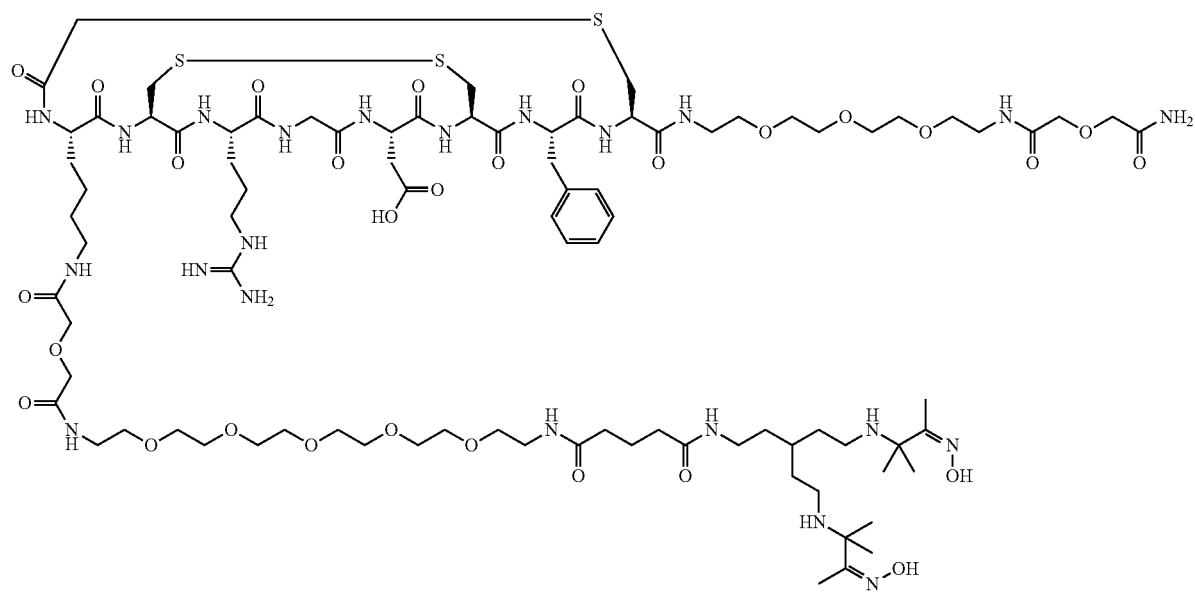 [SMILES: C/C(=N/O)C(C)(C)NCCC(CCNC(=O)CCCC(=O)NCCOCCOCCOCCOCCOCCNC(=O)COCC(=O)NCCCC[C@@H]1NC(=O)CSC[C@@H](C(=O)NCCOCCOCCOCCNC(=O)COCC(N)=O)NC(=O)[C@H](Cc2ccccc2)NC(=O)[C@@H]2CSSC[C@H](NC1=O)C(=O)N[C@@H](CCCNC(=N)N)C(=O)NCC(=O)N[C@@H](CC(=O)O)C(=O)N2)CCNC(C)(C)/C(C)=N\O]

Boc-PEG(6)-Diglycolic acid (50 mg, 0.10 mmol) was coupled to Cys2-6; c[CH$_2$CO-Lys-Cys-Arg-Gly-Asp-Cys-Phe-Cys]-PEG(4)-Diglycoloyl-NH$_2$ (WO 03/006491) (25.2 mg, 0.020 mmol) in DMF using standard coupling reagents (HATU and NMM). The reaction mixture was stirred overnight and concentrated in vacuo. The Boc protection groups were removed by addition of a TFA/water/triisopropylsilane (95:2.5:2.5, 10 mL) solution for 45 min at room temperature. The mixture was concentrated followed by precipitation of crude material from ether. The product was purified by preaffording 3.8 mg. Analysis by LC-MS (column Phenomenex Luna C18(2) 20×2 mm, 3 μm, solvents: A=water/0.1% TFA and B=acetonitrile/0.1% TFA; gradient 15-30% B over 5 min; flow rate 0.6 mL/min, UV detection at 214 and 254 nm, ESI-MS) $t_R$=2.13 min, m/z 1039.0 (MH$_2$)$^{2+}$ confirmed the structure.

Labelling with $^{99m}$Tc was carried out as described in WO 2003/006491.

Example 11

Synthesis of Compound 14

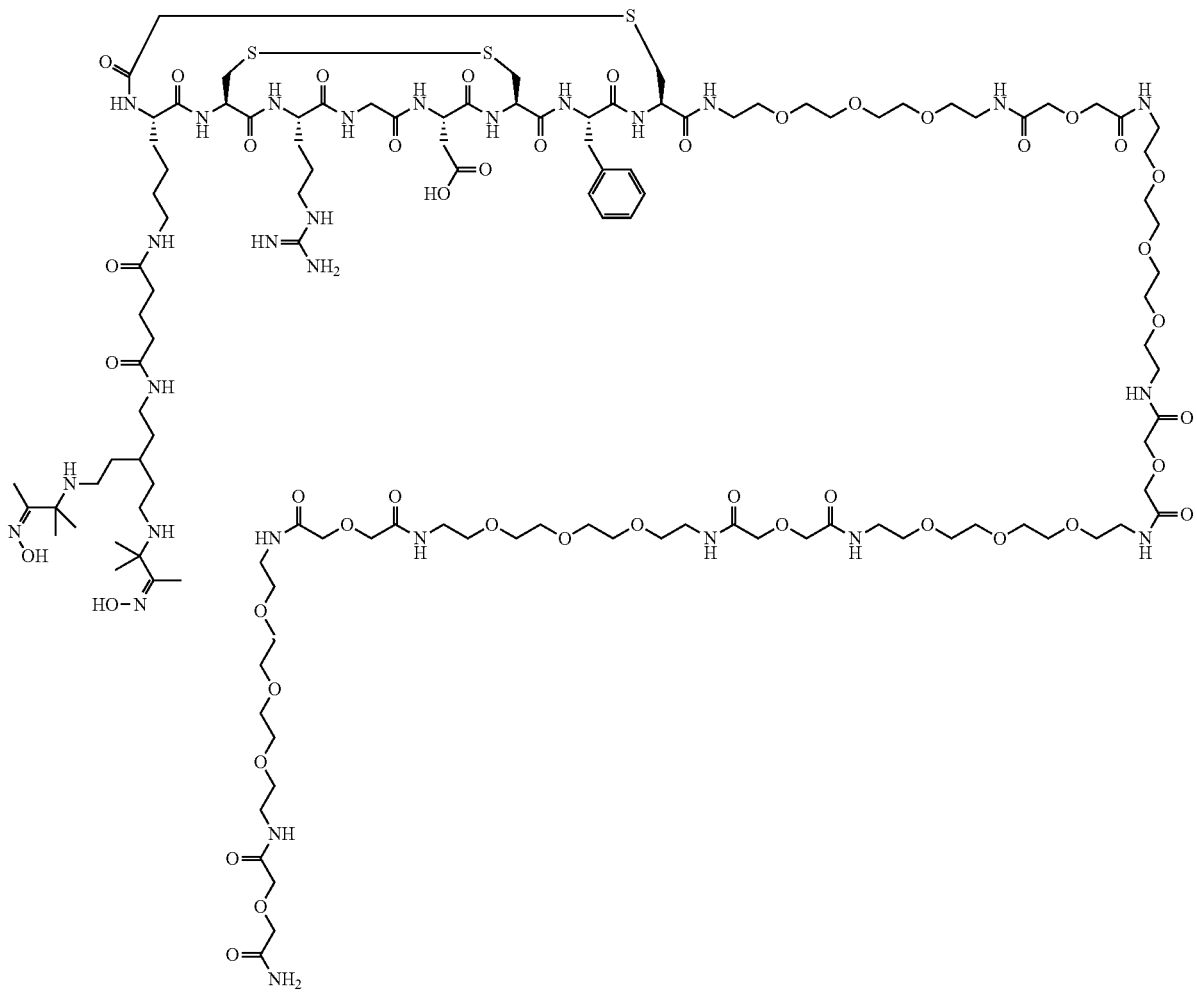 [SMILES: C/C(=N/O)C(C)(C)NCCC(CCNC(=O)CCCC(=O)NCCCC[C@@H]1NC(=O)CSC[C@@H](C(=O)NCCOCCOCCOCCNC(=O)COCC(=O)NCCOCCOCCOCCNC(=O)COCC(=O)NCCOCCOCCOCCNC(=O)COCC(=O)NCCOCCOCCOCCNC(=O)COCC(=O)NCCOCCOCCOCCNC(=O)COCC(N)=O)NC(=O)[C@H](Cc2ccccc2)NC(=O)[C@@H]2CSSC[C@H](NC1=O)C(=O)N[C@@H](CCCNC(=N)N)C(=O)NCC(=O)N[C@@H](CC(=O)O)C(=O)N2)CCNC(C)(C)/C(C)=N\O]

The synthesis was carried out in a manual nitrogen bubbler apparatus on a Rink Amide MBHA resin (loading 0.72 mmol/g) on a 0.80 mmol scale. The Fmoc group on the resin was cleaved by standard protocol. Fmoc-PEG(4)-Diglycolic acid (850 mg, 1.6 mmol) was coupled to the resin using standard coupling reagents (PyAOP and DIEA) in DMF. The conjugation reaction followed by Fmoc deprotection was repeated until 5 PEG(4)-Diglycoloyl groups were introduced on the resin.

Fmoc-Cys(Trt)-OH (1.0 mmol) was coupled to the resin above (0.2 mmol) using standard coupling reagents (PyAOP and NMM) in DMF/dichloromethane (1:1, 6 mL). After 2.5 h an aliquot of the resin was cleaved off (described above) and analysed by LC-MS (column Phenomenex Luna C18(2) 20×2 mm, 3 μm, solvents: A=water/0.1% TFA and B=acetonitrile/0.1% TFA; gradient 10-80% B over 5 min; flow rate 0.6 mL/min, UV detection at 214 and 254 nm, ESI-MS) $t_R$=2.3 min, m/z 1794.1 (MH)$^+$ showing complete conversion.

All subsequent amino acids were coupled using an ABI433A automated peptide synthesiser using SlowMoc coupling protocol on ca 0.1 mmol resin from above to give H-Lys(Boc)-Cys(tBu)-Arg(Pbf)-Gly-Asp(OtBu)-Cys(tBu)-Phe-Cys(Trt)-(PEG(4)-Diglycoloyl)$_5$-Rink amide resin.

Chloroacetic anhydride (2.00 mmol) was synthesised by stirring a solution of chloroacetic acid (378 mg, 4.00 mmol) and DCC (412 mg, 2.00 mmol) in dichloromethane (10 mL) for 1 h followed by filtration. The solution was concentrated and the residue taken up in DMF (3 mL) and added to the peptide resin above. NMM (220 μL, 2.00 mmol) was added and the mixture was left for 3 h. An aliquot of the resin was cleaved (described above) and analysed by LC-MS that confirmed complete conversion. The peptide was cleaved off the resin by addition of a TFA/water/triisopropylsilane solution (95:2.5:2.5, 10 mL) for 3 h. The solution was concentrated.

The residue from above was taken up in water (100 mL) and extracted with ether. To the aqueous solution was added acetonitrile (100 mL) and pH was adjusted to 8 by addition of dilute ammonia. The reaction was left over night. The acetonitrile was evaporated off and the crude product isolated by lyophilisation giving 154 mg. Analysis by LC-MS confirmed complete thioether cyclisation.

Isolated material from above was taken up in a 5% solution of DMSO in TFA (80 mL) and stirred at room temperature for 60 min. The mixture was concentrated and the crude product isolated by precipitation from ether followed by purification by preparative HPLC (column Phenomenex Luna C18(2) 250×21.2 mm, 5 μm, solvents: A=water/0.1% TFA and B=acetonitrile/0.1% TFA; gradient 15-25% B over 60 min; flow rate 10 mL/min, UV detection at 214 and 254 nm) affording 5 mg of pure material. Analysis by LC-MS confirmed the disulfide bridge formation.

Chelate 1-Glutaric acid (WO 03/006491) (9 mg, 0.02 mmol) was coupled to the peptide above using standard coupling reagents (PyAOP and DIEA) in DMF over night. The product was purified by preparative HPLC (column Phenomenex Luna C18(2) 250×21.2 mm, 5 μm, solvents: A=water/0.1% TFA and B=acetonitrile/0.1% TFA; gradient 10-30% B over 60 min; flow rate 10 mL/min, UV detection at 214 and 254 nm) affording 1.3 mg. Analysis by LC-MS (column Phenomenex Luna C18(2) 20×2 mm, 3 μm, solvents: A=water/0.1% TFA and B=acetonitrile/0.1% TFA; gradient 10-60% B over 5 min; flow rate 0.6 mL/min, UV detection at 214 and 254 nm, ESI-MS) $t_R$=1.8 min, m/z 1430.1 $(MH_2)^{2+}$ confirmed the structure.

Labelling with $^{99m}Tc$ was carried out as described in WO 2003/006491.

Example 12

Synthesis of Compound 15 tion (95:2.5:2.5, 10 mL) for 2 h. The solution was concentrated and the crude product isolated by precipitation from ether followed by purification by preparative HPLC (column Phenomenex Luna C18(2) 250×21.2 mm, 5 μm, solvents: A=water/0.1% TFA and B=acetonitrile/0.1% TFA; gradient 20-40% B over 60 min; flow rate 10 mL/min, UV detection at 214 and 254 nm). The semi pure product was isolated by lyophilisation and taken up in 50% acetonitrile/water (6 mL). pH was adjusted to 8 by addition of dilute ammonia and the reaction was stirred overnight. The acetonitrile was evaporated off under reduced pressure and the product isolated by lyophilisation giving 14.8 mg. Analysis by LC-MS [column Phenomenex Luna C18(2) 20×2 mm, 3 μm, solvents: A=water/0.1% TFA and B=acetonitrile/0.1% TFA; gradient 10-60% B over 5 min; flow rate 0.6 mL/min, UV detection at 214 and 254 nm, ESI-MS) $t_R$=2.0 min, m/z 1785.0 $(MH)^+$ confirmed the thioether cyclisation.

The isolated peptide above was taken up in a 5% solution of DMSO in TFA (8 mL) and stirred at room temperature for 15 min. The mixture was concentrated and the crude product precipitated from ether followed by purification by preparative HPLC (column Phenomenex Luna C18(2) 250×10 mm, 10 μm, solvents: A=water/0.1% TFA and B=acetonitrile/0.1% TFA; gradient 10-20% B over 60 min; flow rate 5 mL/min, UV detection at 214 and 254 nm) affording 2 mg

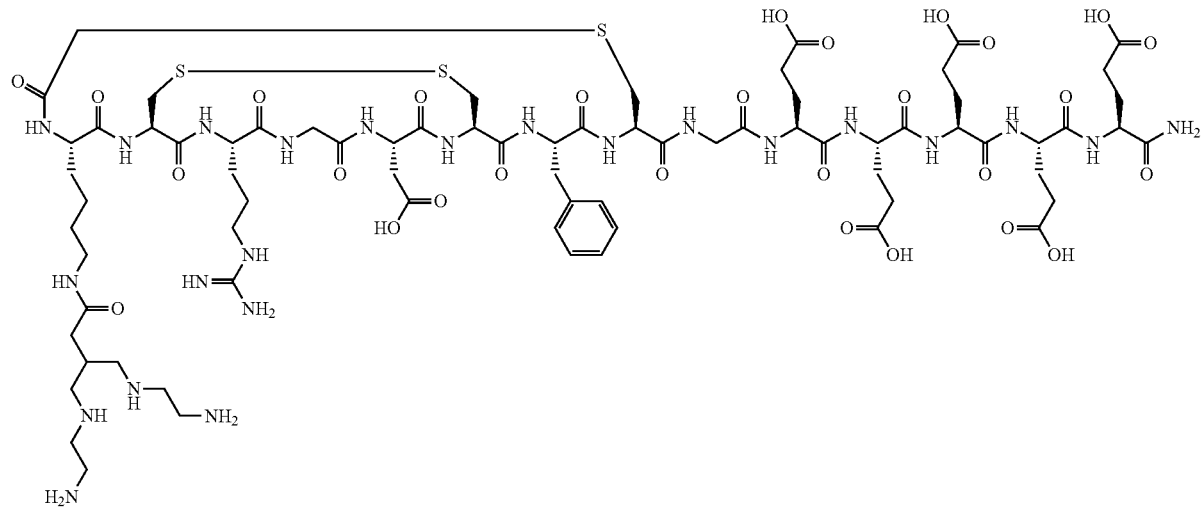 [SMILES: N=C(N)NCCC[C@@H]1NC(=O)[C@@H]2CSSC[C@H](NC(=O)[C@H](CC(=O)O)NC(=O)CNC1=O)C(=O)N[C@@H](Cc1ccccc1)C(=O)N[C@H](C(=O)NCC(=O)N[C@@H](CCC(=O)O)C(=O)N[C@@H](CCC(=O)O)C(=O)N[C@@H](CCC(=O)O)C(=O)N[C@@H](CCC(=O)O)C(=O)N[C@@H](CCC(=O)O)C(N)=O)CSCC(=O)N[C@@H](CCCCNC(=O)CC(CNCCN)CNCCN)C(=O)N2]

The peptide sequence H-Lys(Boc)-Cys(tBu)-Arg(Pbf)-Gly-Asp(OtBu)-Cys(tBu)-Phe-Cys(Trt)-Gly-[Glu(OtBu)]₅—NH₂ was assembled on an ABI 433A automated peptide synthesiser on a Rink amide MBHA resin (0.1 mmol) using SlowMoc coupling method.

A solution of chloroacetic acid (378 mg, 4.00 mmol) and DCC (412 mg, 2.00 mmol) in dichloromethane (10 mL) was stirred at room temperature for 1 h, then filtered and concentrated. The residue was taken up in DMF and added to the peptide resin described above. NMM (220 μl, 2.00 mmol) was added and the reaction left for 2 h. An aliquot of the resin was cleaved (described above) and analysed by LC-MS (column Phenomenex Luna C18(2) 20×2 mm, 3 μm, solvents: A=water/0.1% TFA and B=acetonitrile/0.1% TFA; gradient 20-30% B over 5 min; flow rate 0.6 mL/min, UV detection at 214 and 254 nm, ESI-MS) $t_R$=2.2 min, m/z 1820.7 $(MH)^+$ confirming complete conversion. The peptide was cleaved off the resin by addition of a TFA/water/triisopropylsilane solupure material. Analysis by LC-MS (column Phenomenex Luna C18(2) 20×2 mm, 3 μm, solvents: A=water/0.1% TFA and B=acetonitrile/0.1% TFA; gradient 10-60% B over 5 min; flow rate 0.6 mL/min, UV detection at 214 and 254 nm, ESI-MS) $t_R$=1.0 min, m/z 1670.8 $(MH)^+$ confirmed the peptide.

To a solution of the peptide from above (2 mg, 1 μmol) and Boc-tetraamine-N-hydroxysuccinimide ester (WO 2006/008496) (8.6 mg, 0.012 mmol) in DMF was added DIEA (3 μL, 0.02 mmol). The reaction mixture was stirred overnight and subjected to purification by preparative HPLC (column Phenomenex Luna C18(2) 250×21.2 mm, 5 μm, solvents: A=water/0.1% TFA and B=acetonitrile/0.1% TFA; gradient 20-80% B over 60 min; flow rate 10 mL/min, UV detection at 214 and 254 nm. The pure product was lyophilised and dissolved in a mixture of TFA and dichloromethane (1:1, 2 mL). After 2 h the solvent was evaporated and the residue taken up in acetonitrile/water and lyophilised to afford 1.0 mg of the pure product. Analysis by LC-MS (column Phenomenex Luna C18(2) 20×2 mm, 3 μm, solvents: A=water/0.1% TFA and B=acetonitrile/0.1% TFA; gradient 0-20% B over 5 min; flow rate 0.6 mL/min, UV detection at 214 and 254 nm, ESI-MS) $t_R$=4.2 min, m/z 935.5 $(MH_2)^{2+}$ confirmed the structure.

Labelling with $^{99m}$Tc was carried out as described for Compound 11 in Example 8 above.

What is claimed is:

1. A method to determine the presence, location and/or amount of activated hepatic stellate cells in a subject comprising the following steps:
   (i) providing a subject to whom a detectable quantity of a compound of Formula I has been administered;
   (ii) allowing the compound of Formula I to bind to activated hepatic stellate cells in said subject;
   (iii) detecting signals emitted by said compound of Formula I by an in vivo imaging method; and,
   (iv) generating an image representative of the location and/or amount of said signals;
   wherein said compound of Formula I is defined as follows:

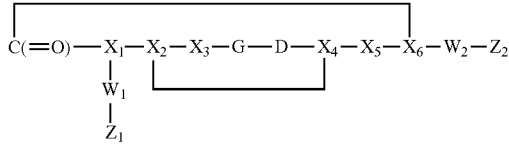

(I)

wherein:
G is glycine;
D is aspartic acid;
$X_1$ is an amino acid selected from aspartic acid, glutamic acid, lysine, homolysine or a $C_{3-6}$ diaminoalkanoic acid;
$X_2$ and $X_4$ are independently amino acid residues whose side chains are linked together to form a cyclising bridge, wherein said amino acid residues are, or wherein when one of $X_2$ and $X_4$ is aspartic acid, the other is lysine;
$X_3$ is arginine or N-methylarginine;
$X_5$ is tyrosine, phenylalanine, 3-iodo-tyrosine $C_{4-6}$ cycloalkylalanine or naphthylalanine;
$X_6$ is a thiol-containing amino acid that forms either a thioether bond or a thioacetal bond linking $X_6$ to the C(=O) group;
$W_1$ and $W_2$ are independently absent or a linker moiety, wherein when present $W_1$ is linked to the amino acid side chain moiety of $X_1$ and $W_2$ when present is linked to the carboxy group of $X_6$; and,
$Z_1$ and $Z_2$ are independently an imaging moiety, a sugar moiety, a cyanine dye or hydrogen, with the proviso that at least one of $Z_1$ and $Z_2$ is an imaging moiety.

2. The method of claim 1 wherein for said compound of Formula I:
$X_1$ is lysine;
$X_2$ and $X_4$ are both cysteine;
$X_3$ is arginine;
$X_5$ is phenylalanine; and,
$X_6$ is cysteine.

3. The method of claim 1 wherein for said compound of Formula I at least one of $W^1$ and $W^2$ is present and said linker moiety is a radical of Formula -(L)$_n$- wherein:
each L is independently —C(=O)—, —CR'$_2$—, —CR'=CR'—, —C≡C—, —CR'$_2$CO$_2$—, —CO$_2$CR'$_2$—, —NR'—, —NR'CO—, —CONR'—, —NR'(C=O)NR'—, —NR'(C=S)NR'—, —SO$_2$NR'—, —NR'SO$_2$—, —CR'$_2$OCR'$_2$—, —CR'$_2$SCR'$_2$—, —CR'$_2$NR'CR'$_2$—, a $C_{4-8}$ cycloheteroalkylene group, a $C_{4-8}$ cycloalkylene group, a $C_{5-12}$ arylene group, a $C_{3-12}$ heteroarylene group, an amino acid, a polyalkyleneglycol, polylactic acid or polyglycolic acid moiety;
n is an integer of value 1 to 15;
each R' group is independently H or $C_{1-10}$ alkyl, $C_{3-10}$ alkylaryl, $C_{2-10}$ alkoxyalkyl, $C_{1-10}$ hydroxyalkyl, $C_{1-10}$ fluoroalkyl, or 2 or more R' groups, together with the atoms to which they are attached form a carbocyclic, heterocyclic, saturated or unsaturated ring.

4. The method of claim 1 wherein for said compound of Formula I at least one of $W^1$ and $W^2$ is present and said linker moiety is a monodisperse PEG building block comprising 1 to 10 units of said building block.

5. The method of claim 1 compound of wherein for said compound of Formula I at least one of $W^1$ and $W^2$ is present and said linker moiety is 1 to 10 amino acid residues.

6. The method of claim 1 wherein for said compound of Formula I one of $Z_1$ and $Z_2$ is a sugar moiety.

7. The method of claim 1 wherein for said compound of Formula I one of $Z_1$ and $Z_2$ is a cyanine dye moiety.

8. The method of claim 1 wherein said imaging moiety is selected from:
   (i) a radioactive metal ion;
   (ii) a gamma-emitting radioactive halogen;
   (iii) a positron-emitting radioactive non-metal; and,
   (iv) a paramagnetic metal ion.

9. The method of claim 8 wherein said imaging moiety is selected from (i) to (iii).

10. The method of claim 9 wherein said imaging moiety is selected from $^{99m}$Tc, $^{123}$I, $^{11}$C and $^{18}$F.

11. The method of claim 1 wherein said compound of Formula I is part of a pharmaceutical composition comprising said compound of Formula I together with a biocompatible carrier, wherein said pharmaceutical composition is in a form suitable for mammalian administration.

12. The method of claim 1 wherein said subject is an intact mammalian body in vivo.

13. The method of claim 1 wherein said subject is a human.

* * * * *